US005695956A

United States Patent [19]

McClane et al.

[11] Patent Number: 5,695,956
[45] Date of Patent: Dec. 9, 1997

[54] CLOSTRIDIUM PERFINGENS TYPE A ENTEROTOXIN TOXOID AND METHODS OF PREPARATION AND USE AS A VACCINE AND THERAPEUTIC AGENT

[75] Inventors: Bruce A. McClane, Pittsburgh, Pa.; Philip C. Hanna, Charlestown, Mass.; Timothy A. Mietzner, Pittsburgh, Pa.

[73] Assignee: University of Pittsburgh of the Commonwealth System of Higher Education, Pittsburgh, Pa.

[21] Appl. No.: 213,452

[22] Filed: Mar. 15, 1994

Related U.S. Application Data

[63] Continuation of Ser. No. 874,982, Apr. 22, 1992, abandoned, which is a continuation of Ser. No. 618,541, Nov. 26, 1990, abandoned.

[51] Int. Cl.$^6$ .................................................... C12P 21/02
[52] U.S. Cl. .................. 435/69.1; 435/71.1; 435/91.1; 435/252.3; 435/252.33; 536/23.1
[58] Field of Search ........................... 435/6, 69.1, 71.1, 435/91.1, 91.32, 172.3, 252.3, 252.33, 270, 320.1; 536/23.1

[56] References Cited

U.S. PATENT DOCUMENTS

| | | | |
|---|---|---|---|
| 4,264,588 | 4/1981 | Orcutt | 424/92 |
| 4,292,307 | 9/1981 | Zemlyakova | 424/92 |
| 4,689,299 | 8/1987 | Insel et al. | 435/240.27 |

OTHER PUBLICATIONS

"The 31 C–Term Amino Acids of *Clostridium perfringens* Enterotoxin Defines the Receptor Binding Domain", poster displayed at Annual Meeting of American Society for Microbiology, Anaheim, California (May 1990), P. C. Hanna and B. A. McClane Abstract.

"A recombinant C–terminal toxin fragment provides evidence that membrane insertion is important for *Clostridium perfringens* enterotoxin cytotoxicity", *Molecular Biology*, vol. 5, No. 1, pp. 225–230 (Jan. 1991),Philip C. Hanna and Bruce A. McClane.

"Localization of the Receptor–binding Region of *Clostridium perfringens* Enterotoxin Utilizing Cloned Toxin Fragments and Synthetic Peptides", *Journal of Biological Chemistry*, vol. 266, No. 17, pp. 11037–11043 (Jun. 1991), Philip C. Hanna, Timothy A. Mietzner, Gary K. Schoolnik and Bruce A. McClane.

"Isolation and Function of a *Clostridium perfringens* Enterotoxin Fragment" *Infection and Immunity*, vol. 55, No. 12, pp. 2912–2915 (Dec. 1987), Yas uhiko Horiguchi, Tetsuo Akai, and Genji Sakaguchi.

"Molecular Cloning of the 3' Half of the *Clostridium perfringens* Enterotoxin Gene and Demonstration that This Region Encodes Receptor–Binding Activity", *Journal of Bacteriology*, vol. 171, No. 12, pp. 6815–6820 (Dec. 1989) Philip C. Hanna, Andrew P. Wnek, and Bruce A. McClane.

Van Damme–Jongsten et al., Antonic van Leeuwenhoek, 56(2): 181–190, 1989.

Amicon, Centricon Microconcentrators Operating Instructions.

Crowl, et al Gene 38:31–38 1985.

McClane et al J Clin Micro 19(2):112–115 1984.

Popoff FEMS Micro Lett 21:1–5 1984.

Current Protocols in Molecular Biology Wiley & Sons Publisher 1987 chapters 1–3 & 6.

Hanna, et al J. Bacteriology 171(12) 6815–6820 1989.

Van Damme–Jongsten, et al., 1990, Snythetic DNA Probes for Detection of Enterotoxigenic *Clostridium perfingens* Strains Isolated from Outbreaks of Food Poisoning, J. Clin. Micro. 28 (1): 131–133.

Van Damme–Jongsten, et al., 1990, Testing strains of *Clostridium perfringens* type A isolted from diarrhoeic piglets for the presence of the enterotoxin gene, Veterinary record 126: 191–192.

Iwanejko, et al., 1989 Cloning in *Escherichia coli* of the Enterotoxin Gene from *Clostridium perfringens* Type A, J. Gen. Microbiology 135: 903–909.

Granum, 1986, Structure and Mechanism of Action of the Enterotoxin from *Clostridium Perfringes*. In: Falmagney, P, et al, ed. Second European Workshop on bacterial protein toxins, 327–343.

Richardson & Granum, 1985, The amino acid sequence of the enterotoxin from *Clostridium perfringes* type A, FEBS Letters 182 (2): 479–484.

Ricardson & Granum, 1983, sequence of the Amino–Terminal Part of Enterotoxin from *Clostridium perfringes* Type A Identification of Points of Trypsin Activation, Infection and Immunity 40 (3): 943–949.

Granum, 1982, Inhibition of Proteins Synthesis by a Tryptic Polypeptide of *Clostridium Perfringes* Type A Enterotoxin, Biochim. Biophys. Acta. 708: 6–11.

Granum, et al., 1981, Tryspin Activation of Enterotoxin from *Clostridium Perfringesn* Type A, Biochim. Biophys. Acta. 668: 325–332.

*Primary Examiner*—Christine M. Nucker
*Assistant Examiner*—Laurie Scheiner
*Attorney, Agent, or Firm*—Eckert Seamans Cherin & Mellott, LLC

[57] ABSTRACT

*Escherichia coli* strains that produce recombinant *Clostridium perfringens* type A enterotoxin toxoids from a *Clostridium perfringens* type A enterotoxin gene fragment encoding the *Clostridium perfringens* type A enterotoxin binding domain subcloned into an expression vector for forming plasmids are disclosed. The *Clostridium perfringens* type A enterotoxin toxoids of this invention recognize, irreversibly bind to and saturate receptor sites on intestinal membranes and, thus effectively compete for these receptor sites with *Clostridium perfringens* type A enterotoxin. The toxoids of this invention may be used to treat the symptoms of *Clostridium perfringens* food poisoning in patients. Vaccines are also disclosed that may be used to prevent the symptoms of *Clostridium perfringens* food poisoning in patients. Processes for preparing the plasmids and toxoids of this invention and for using the toxoids and vaccines of this invention are also provided.

15 Claims, 13 Drawing Sheets

Construction of plasmid vectors containing the *cpe* gene insert. A 2.3 kilobase (Kb) insert was excised from λph161 with EcoR1 and subcloned into pGEM4 (generating pPH100) or into expression vector pEV-vrfl (generating pPH300). pPH200 is the result of subcloning of a 200-base-pair *Sma* I (located in the MCS)- *Hind* III insert from pPH100 into pGEM4.

```
             TTA GGA AAT ATT GAT CAA GGT TCA TTA ATT GAA ACT GGT GAA AGA   45
NH2 — Leu Gly Asn Ile Asp Gln Gly Ser Leu Ile Glu Thr Gly Glu Arg
       1               5                  10                 15

TGT GTT TTA ACA GTT CCA TCT ACA GAT ATA GAA AAA GAA ATC CTT   90
     Cys Val Leu Thr Val Pro Ser Thr Asp Ile Glu Lys Glu Ile Leu
                      20                 25                 30

GAT TTA GCT GCT GCT ACA GAA AGA TTA AAT TTA ACT GAT GCA TTA  135
     Asp Leu Ala Ala Ala Thr Glu Arg Leu Asn Leu Thr Asp Ala Leu
                      35                 25                 45

AAC TCA AAT CCA GCT GGT AAT TTA TAT GAT TGG CGT TCT TCT AAC  180
     Asn Ser Asn Pro Ala Gly Asn Leu Tyr Asp Trp Arg Ser Ser Asn
                      50                 55                 60

TCA TAC CCT TGG ACT CAA AAG CTT AAT TTA CAC TTA ACA ATT ACA  225
     Ser Tyr Pro Trp Thr Gln Lys Leu Asn Leu His Leu Thr Ile Thr
                      65                 70                 75

GCT ACT GGA CAA AAA TAT AGA ATC TTA GCT AGC AAA ATT GTT GAT  270
     Ala Thr Gly Gln Lys Tyr Arg Ile Leu Ala Ser Lys Ile Val Asp
                      80                 85                 90

TTT AAT ATT TAT TCA AAT AAT TTT AAT AAT CTA GTG AAA TTA GAA  315
     Phe Asn Ile Tyr Ser Asn Asn Phe Asn Asn Leu Val Lys Leu Glu
                      95                100                105

CAG TCC TTA GGT GAT GGA GTA AAA GAT CAT TAT GTT GAT ATA AGC  360
     Gln Ser Leu Gly Asp Gly Val Lys Asp His Tyr Val Asp Ile Ser
                     110                115                120

TTA GAT GCT GGA CAA TAT GTT CTT GTA ATG AAA GCT AAT TCA TCA  405
     Leu Asp Ala Gly Gln Tyr Val Leu Val Met Lys Ala Asn Ser Ser
                     125                130                135

TAT AGT GGA AAT TAC CCT TAT TCA ATA TTA TTT CAA AAA TTT TAA  450
     Tyr Ser Gly Asn Tyr Pro Tyr Ser Ile Leu Phe Gln Lys Phe *** — COOH
                     140                145                150
```

FIG. 4

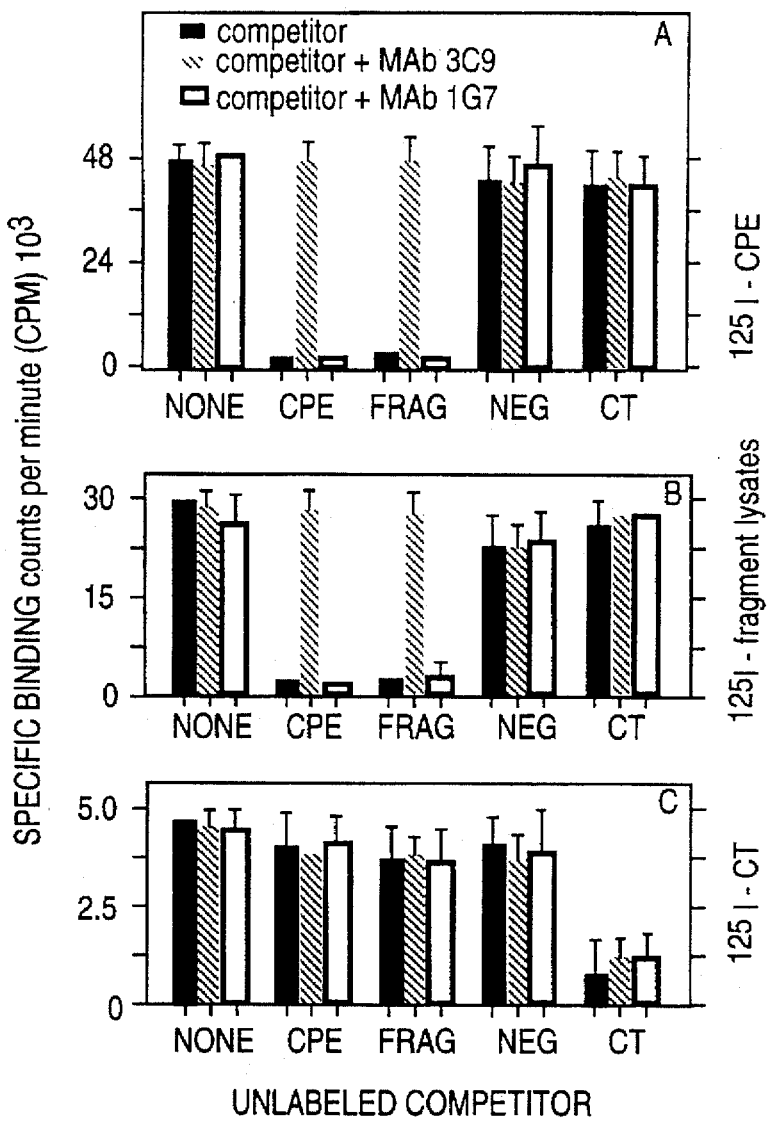

Summary of competitive-binding studies. Brush border membranes were preincubated as follows with unlabeled competitors (ordinate) : NONE, Dulbecco modified phosphate-buffered saline contrtol; Clostridium perfringens type A enterotoxin (CPE) 25ug of protein; Clostridium perfringens type A entertoxin gene fragment of amino acids 171-319 (FRAG) 300µg of protein from concentrated FRAG lysates; 300µg of protein from concentrated negative control lysates (NEG); 50µg of cholera toxin protein (CT). Brush border membranes were then assayed as follows for specific binding of $^{125}$I-labeled ligands: A [$^{125}$I] CPE (0.5 ug); B, $^{125}$I-labeled FRAG lysates (150 µg); C, [$^{125}$I] CT (1µg). Unlabeled competitors were also preincubated for 15 minutes at 37°C with 500µg of MAb3C9 (cross-hatched bars) or MAb1G7 (open bars) to demonstrate specificity of fragment binding. Error bars represent standard errors of the means (n=4).

FIG. 7

Hindlll (H3) Restriction Map of pPH600

Construction of plasmid pPH600
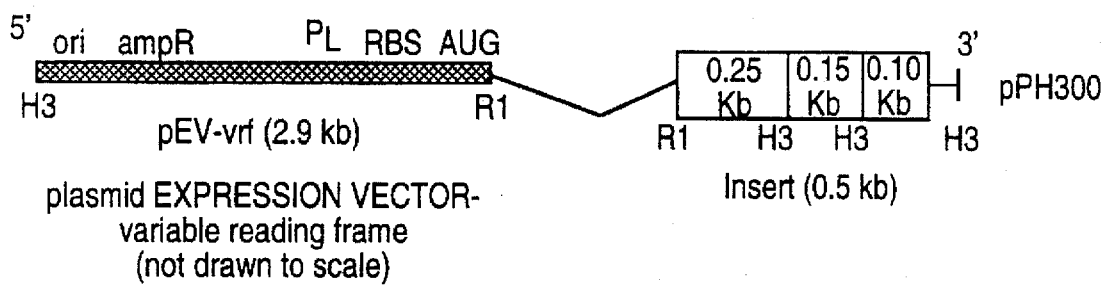
pPH300 was digested with Hind III (H3) to completion. The digested DNA was then separated on an agarose gel and the small 0.1 Kb piece was isolated and ligated into the Hind III site of the vector pEV-vrf to yield the construct pPH600 shown below.
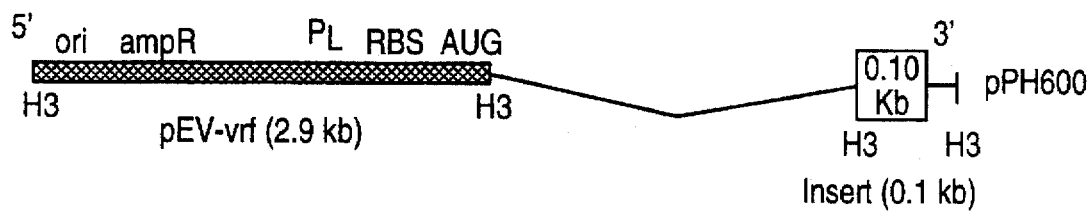
FIG. 10

NH2- SER LEU ASP ALA GLY GLN TYR
                          5

VAL LEU VAL MET LYS ALA ASN
         10

SER SER TYR SER GLY ASN TYR
 15                      20

PRO TYR SER ILE LEU PHE GLN
             25

LYS PHE - COOH
 30

FIG. 13

[1]Conjugate = synthetic peptide conjugated to thyroglobulin.

CLOSTRIDIUM PERFRINGENS TYPE A ENTEROTOXIN TOXOID AND METHODS OF PREPARATION AND USE AS A VACCINE AND THERAPEUTIC AGENT

This is a continuation of application Ser. No. 07/874,982, filed Apr. 22, 1992 now abandoned, which is a continuation of application Ser. No. 07/618,541, filed Nov. 26, 1990 now abandoned.

BACKGROUND OF THE INVENTION

The invention described herein was made in the course of work supported in part by Public Health Service, grant No. 2 R01 AI19844-07 from the National Institutes of Health, National Institute of Allergy and Infectious Diseases. The Government has certain rights in this invention.

The following microorganisms have been deposited by Bruce A. McClane on behalf of the University of Pittsburgh of the Commonwealth System of Higher Education, Pittsburgh, Pa. 15260, U.S.A. on Nov. 9, 1990, with and are available from the permanent collection of the American Type Culture Collection (ATCC), 12301 Parklawn Drive, Rockville, Md. 20852-1776, U.S.A.:

| ATCC 55121 | *E. coli* Y1089 lysogenized with Lambda ph161 |
|---|---|
| ATCC 68474 | *E. coli* RR1 (pPH300) |
| ATCC 68475 | *E. coli* RR1 (pPH600) |

The American Type Culture Collection has performed viability tests on each of the hereinbefore mentioned deposited microorganisms and has concluded on Nov. 13, 1990 that each of the hereinbefore mentioned deposited microorganisms is viable and capable of reproduction.

These deposits are available to the public upon the grant of a patent to the assignee, the University of Pittsburgh of the Commonwealth System of Higher Education, disclosing them. However, it should be understood that the availability of these deposits does not constitute a license to practice this invention in derogation of patent rights granted by governmental action.

Field of the Invention

This invention relates to recombinant *Clostridium perfringens* type A enterotoxin toxoids, a method of producing these toxoids, a method of using these toxoids as vaccines in patients as a prophylactic measure to prevent the development of *Clostridium perfringens* food poisoning, and a method for using these toxoids in patients to treat the symptoms associated with food poisoning due to *Clostridium perfringens*. The invention relates to the characterization of the 3' half of the *Clostridium perfringens* type A enterotoxin gene. More specifically, this invention relates to the cloning of the 3' half of the *Clostridium perfringens* type A enterotoxin gene into an *Escherichia coli* expression vector using recombinant techniques to allow for the production of a plasmid encoding a toxoid. This plasmid is capable of producing a *Clostridium perfringens* type A enterotoxin toxoid. This invention provides a toxoid produced from a defined *Clostridium perfringens* type A enterotoxin gene fragment encoding amino acids 171 through 319 of intact *Clostridium perfringens* enterotoxin. SEQ ID NO:1 in the SEQUENCE LISTING sets forth the base codes as triplets and the amino acid sequence for the *Clostridium perfringens* type A enterotoxin gene fragment encoding amino acids 171 through 319 of intact *Clostridium perfringens* type A enterotoxin. Production of this toxoid is free from contamination with intact *Clostridium perfringens* type A enterotoxin or other *Clostridium perfringens* type A enterotoxin fragments. More specifically, this invention provides a toxoid from a defined *Clostridium perfringens* type A enterotoxin gene fragment encoding amino acids 171 through 319 that recognizes, irreversibly binds to and saturates receptor sites on intestinal membranes, thus, competing for these sites with *Clostridium perfringens* type A enterotoxin. The toxoid of this invention is nontoxic to mammalian cells. The recombinant toxoid produced by plasmid pPH300 may be used in patients as a vaccine for prevention of disease caused by *Clostridium perfringens* type A enterotoxin, or as a therapeutic agent to treat the symptoms of food poisoning due to *Clostridium perfringens* type A enterotoxin. Another embodiment of this invention provides a toxoid produced from a defined *Clostridium perfringens* type A enterotoxin gene fragment encoding amino acids 290 through 319 of intact *Clostridium perfringens* enterotoxin. Production of this toxoid is free from contamination of intact *Clostridium perfringens* type A enterotoxin or other *Clostridium perfringens* type A enterotoxin fragments. This invention provides a toxoid from a defined *Clostridium perfringens* type A enterotoxin gene fragment encoding amino acids 290 through 319 that recognizes, irreversibly binds to and saturates receptor sites on intestinal membranes, thus, competing for these sites with *Clostridium perfringens* type A enterotoxin. This toxoid is nontoxic to mammalian cells. The recombinant toxoid produced by plasmid pPH600 may be used in patients for the prophylaxis or treatment of symptoms associated with *Clostridium perfringens* food poisoning. A synthetic peptide based on the translated DNA sequence of plasmid pPH600 containing *Clostridium perfringens* type A enterotoxin gene fragment encoding amino acids 290 through 319 is provided for in this invention. SEQ ID NO:2 in the SEQUENCE LISTING sets forth the amino acid sequence of this synthetic peptide.

Brief Description of the Prior Art

*Clostridium perfringens* type A enterotoxin is responsible for the symptoms associated with *Clostridium perfringens* food poisoning and may also be involved in other human and veterinary gastrointestinal illnesses. These symptoms may include, for example, diarrhea and intestinal cramping. *Clostridium perfringens* food poisoning is generally self-limiting in healthy adult patients, although death may occur in patients compromised by age extremes or pre-existing illnesses or other physical conditions. It has been known that *Clostridium perfringens* type A enterotoxin is a single polypeptide chain of approximately 35 kilodaltons (kDa) which has no significant amino acid homology with other enterotoxins.

It is generally known by those persons skilled in the art that *Clostridium perfringens* type A enterotoxin binds to specific eucaryotic receptors which may include two membrane proteins of 50 and 70 kilodaltons (kDa). After binding, *Clostridium perfringens* type A enterotoxin is inserted into the plasma membrane to rapidly produce significant changes in membrane ion permeability. It has also been known that these changes in ion permeability result in later secondary *Clostridium perfringens* type A enterotoxin effects, such as, for example, inhibition of macromolecular synthesis and morphologic damage.

It is well known that assignment of specific functions to defined regions of toxin molecules may be used to gain insight into toxin action. Further, it has been known to define receptor-binding domains of a toxin to form a rational basis for designing more effective toxoids for vaccination and therapeutic purposes.

It is generally known by those persons skilled in the art that a toxoid is an inactivated derivative of a biologically active toxin. Often, these toxoids retain antigenicity and are useful as vaccines. It has been known that nonrecombinant toxoids may be prepared by chemical inactivation of intact toxin molecules produced by the pathogen. Vaccines using these nonrecombinant toxoids often retain toxicity due to incomplete chemical inactivation or contamination with other toxic components produced during toxoid preparation or from the pathogen itself.

U.S. Pat. No. 4,264,588 discloses a vaccine for *Clostridium perfringens* type E enterotoxemia of rabbits. This patent discloses a method for producing a vaccine for *Clostridium perfringens* type E enterotoxemia of rabbits including adding a proteolytic enzyme to a supernatant fluid of *Clostridium perfringens* type E protein to produce a proteinaceous toxin having a molecular weight of from 70,000 to 80,000 daltons, and then adding a fixing agent to inactivate the toxin to produce a toxoid. A process of vaccinating rabbits with a vaccine for *Clostridium perfringens* type E enterotoxemia of rabbits is also disclosed. It will be appreciated by those persons skilled in the art that the vaccine of this patent involves production of a toxoid using a different *Clostridium perfringens* toxin than *Clostridium perfringens* type A enterotoxin, and thus, this patent will not protect against disease produced by *Clostridium perfringens* type A enterotoxin.

U.S. Pat. No. 4,292,307 discloses a vaccine for the prophylaxis and treatment of clostridioses of animals and poultry comprising formaldehyde-detoxicated toxoids of *Clostridium perfringens* type A, B and D, *C. oedematiens*, *Clostridium septicum*, *Clostridium tetani* and *Clostridium botulinum* type A, B, C, D, E and F. This patent also provides a method for the prophylaxis and treatment of clostridioses of animals and poultry. This patent employs the chemical inactivation approach to vaccine production.

U.S. Pat. No. 4,689,299 discloses a protective human monoclonal antibody against tetanus toxin or diptheria toxin, as well as other bacterial toxins such as *Clostridium perfringens*. This patent provides a method for producing human monoclonal antibodies against bacterial toxins, including tetanus toxin, diptheria toxin, and *Clostridium perfringens* toxin, by fusing readily accessible human peripheral blood lymphocytes with murine myeloma cell lines deficient in murine antibody production. This patent states that human monoclonal antibodies synthesized by these fused cell hybrids (hybridomas) can be administered in a solution to infected or potentially infected individuals to resist the onset of toxin-induced disease. This patent discloses the isolation of clones and antibody detection but does not involve toxoid production.

"Isolation and Function of a *Clostridium perfringens* Enterotoxin Fragment", *Infection and Immunity*, Vol. 55, No. 12, pp. 2912-2915 (December 1987), Yasuhiko Horiguchi, Tetsuo Akai and Genji Sakaguchi, discloses a chemically produced *Clostridium perfringens* enterotoxin fragment that was obtained by treating intact *Clostridium perfringens* enterotoxin with 2-nitro-5-thiocyanobenzoic acid. This article states that 2-nitro-5-thiocyanobenzoic acid chemically cleaves the amino-terminal peptide bond of cysteine residues. This article does not disclose the production of toxoids.

In spite of these prior art disclosures, there remains a very real and substantial need for *Clostridium perfringens* type A enterotoxin toxoids that have no possibility of residual *Clostridium perfringens* type A enterotoxin activity, a method of using these toxoids therapeutically as a treatment for the symptoms of food poisoning due to *Clostridium perfringens* type A enterotoxin, a method of using these toxoids as vaccines to prevent the symptoms of food poisoning due to *Clostridium perfringens* type A enterotoxin, and a method of preparing these toxoids that does not involve production of intact *Clostridium perfringens* type A enterotoxin and that has no possibility of residual *Clostridium perfringens* type A enterotoxin activity to produce the symptoms associated with *Clostridium perfringens* food poisoning.

BRIEF DESCRIPTION OF THE DRAWINGS

FIG. 4 shows the DNA sequence (top line of each horizontal row) and the derived amino acid sequence (bottom lines of each horizontal row) for the *Clostridium perfringens* type A enterotoxin gene fragment encoding amino acids 171 through 319, SEQ ID NO:1.

FIG. 7 shows a summary of competitive binding studies. Brush border membranes were preincubated as follows with unlabeled competitors (ordinate): NONE, Dulbecco modified phosphate-buffered saline control; *Clostridium perfringens* type A enterotoxin (CPE) 25 µg of protein; *Clostridium perfringens* type A enterotoxin (CPE) fragment of amino acids 171-319 (FRAG) 300 µg of protein from concentrated FRAG lysates; 300 µg of protein from concentrated negative control lysates (NEG); 50 µg of cholera toxin protein (CT). Brush border membranes were then assayed as follows for specific binding of $^{125}$I-labeled ligands: A [$^{125}$I] CPE (0.5 µg); B, $^{125}$-labeled FRAG lysates (150 µg); C, [$^{125}$I] CT (1 µg). Unlabeled competitors were also preincubated for 15 minutes at 37° C. with 500 µg of MAb3C9 (cross-hatched bars) or MAb1G7 (open bars) to demonstrate specificity of fragment binding. Error bars represent standard errors of the means (n=4).

FIG. 10 shows the construction of recombinant plasmid pPH600.

FIG. 13 shows the amino acid sequence of a synthetic peptide, SEQ ID NO:2.

Figure 1:
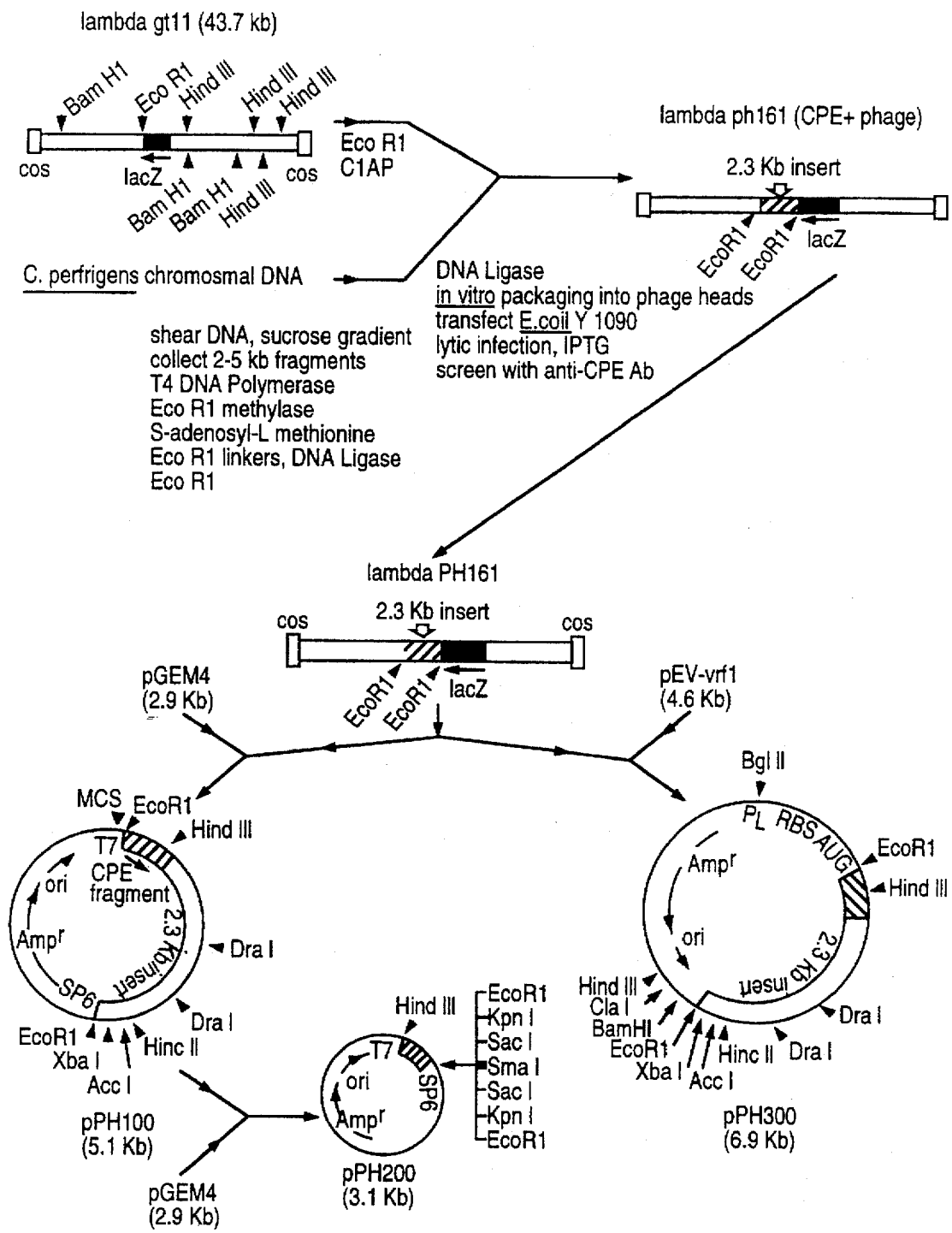
FIG. 1 shows the construction of positive-scoring plaque lambda ph161 and recombinant plasmid pPH300.

It will be appreciated that the restriction endonuclease abbreviations set forth in FIGS. 1, 2, 9 and 10 are all standard and well known by those persons skilled in the art.

SUMMARY OF THE INVENTION

The present invention has met the hereinbefore described need. The present invention provides a recombinant DNA plasmid or bacteriophage transfer vector having an *Escherichia coli* expression vector and a DNA sequence encoding for a *Clostridium perfringens* type A enterotoxin gene fragment that produces a *Clostridium perfringens* type A enterotoxin receptor binding domain. The present invention provides a toxoid produced by a recombinant plasmid in an *Escherichia coli* strain. This plasmid contains a *Clostridium perfringens* type A enterotoxin gene fragment encoding amino acids 171 through 319 that constitutes the toxoid. This plasmid contains the *Escherichia coli* expression vector regulatory regions and the *Clostridium perfringens* type A enterotoxin gene fragment and is capable of producing a toxoid. This plasmid is designated pPH300. The toxoid of this invention recognizes, irreversibly binds to and saturates receptor sites on intestinal membranes and thus effectually competes for those sites with *Clostridium perfringens* type A enterotoxin. The toxoid of this invention is nontoxic to mammalian cells. This toxoid may be used as a vaccine for preventing the symptoms associated with food poisoning in patients due to *Clostridium perfringens* type A enterotoxin. The toxoid of this invention may be used to provide a treatment for the symptoms associated with food poisoning in patients due to *Clostridium perfringens* type A enterotoxin.

More specifically, this invention provides a continuous *Escherichia coli* strain that produces a recombinant *Clostridium perfringens* type A enterotoxin toxoid from a *Clostridium perfringens* type A enterotoxin gene fragment encoding amino acids 290 through 319 subcloned into an *Escherichia coli* expression vector for forming a plasmid. This plasmid contains the *Escherichia coli* expression vector regulatory regions and the *Clostridium perfringens* type A enterotoxin gene fragment and is capable of producing the toxoid. This plasmid is designated pPH600. The toxoid of this invention recognizes, irreversibly binds to and saturates receptor sites on intestinal membranes, and thus effectively competes for these sites with *Clostridium perfringens* type A enterotoxin. This toxoid is nontoxic to mammalian cells. This toxoid may be used as a vaccine in patients for the prophylaxis of the symptoms associated with food poisoning due to *Clostridium perfringens* type A enterotoxin. This toxoid may be used in patients as a treatment for the symptoms associated with food poisoning due to *Clostridium perfringens* type A enterotoxin.

Further, this invention provides a process for preparing a *Clostridium perfringens* type A enterotoxin toxoid including generating a recombinant λgt11 library of *Clostridium perfringens* (*C. perfringens*) DNA, screening this library with an anti-*Clostridium perfringens* type A enterotoxin monoclonal antibody MAb3C9 to obtain a positive scoring plaque designated lambda ph161 (λph161) that contains a *Clostridium perfringens* type A enterotoxin gene fragment encoding amino acids 171 through 319, subcloning lambda ph161 into plasmid pEV-vrf1 to obtain a recombinant *Clostridium perfringens* type A enterotoxin toxoid producing plasmid pPH300, transforming plasmid pPH300 into an *Escherichia coli* RR1, growing the *Escherichia coli* RR1 harboring plasmid pPH300 under suitable conditions to produce cultures having the toxoid, employing centrifugation upon the cultures for the harvesting of cells, re-suspending the cells in a suitable medium, lysing the cells, and removing debris from the cells for the production of soluble lysates containing nontoxic *Clostridium perfringens* type A enterotoxin toxoid. Subsequent to removal of cellular debris from the bacterial lysate, the *C. perfringens* type A enterotoxin toxoid can be concentrated and partially purified by subjecting the bacterial lysate to about a 40% $(NH_4)_2SO_4$ solution for the precipitation of a pellet fraction containing the *C. perfringens* type A enterotoxin toxoid. The *C. perfringens* type A enterotoxin toxoid may also be purified and concentrated by a process of initially subjecting the bacterial lysate to the 40% $(NH_4)_2SO_4$ solution discussed above, followed by an additional precipitation of the remaining bacterial lysate by addition of a 15% $(NH_4)_2SO_4$ solution. The second pellet fraction contains the *C. perfringens* type A enterotoxin toxoid.

Further, this invention provides a process for preparing a *Clostridium perfringens* type A enterotoxin toxoid that may be expressed from plasmid pPH600 and that contains a *Clostridium perfringens* type A enterotoxin gene fragment encoding amino acids 290 through 319.

Additionally, this invention provides a synthetic peptide based on the amino acid sequence deduced from the DNA sequence of plasmid pPH600 containing *Clostridium perfringens* type A enterotoxin gene fragment encoding amino acids 290 through 319.

It is an object of the present invention to provide an *Escherichia coli* strain serving as a continuous source of a recombinant *Clostridium perfringens* type A enterotoxin toxoid that is nontoxic to mammalian cells and that has a *Clostridium perfringens* type A enterotoxin gene fragment encoding amino acids 171 through 319 that recognizes, irreversibly binds to, and saturates receptor sites on intestinal membranes and thus effectively competes for these sites with toxic *Clostridium perfringens* type A enterotoxin.

It is an object of the present invention to provide an *Escherichia coli* strain serving as a continuous source of a recombinant *Clostridium perfringens* type A enterotoxin toxoid that is nontoxic to mammalian cells and that has a *Clostridium perfringens* type A enterotoxin gene fragment encoding the carboxy-terminal amino acids 290 through 319 that effectively competes with *Clostridium perfringens* type A enterotoxin for specific binding sites on mammalian intestinal brush border membranes and that protects mammalian cells from subsequent *Clostridium perfringens* type A enterotoxin challenge.

It is an object of this invention to provide a process for obtaining a positive-scoring plaque lambda ph161 and for constructing and preparing recombinant plasmids pPH300 and pPH600.

It is an object of the present invention to provide a synthetic peptide derived from the DNA sequence data of recombinant plasmid pPH600.

It is an object of this invention to provide a toxoid that may be used as a vaccine for the prophylaxis of food poisoning in patients due to *Clostridium perfringens* type A enterotoxin.

It is an object of the present invention to provide a toxoid that may be used for the treatment of the symptoms associated with food poisoning in patients due to *Clostridium perfringens* type A enterotoxin.

It is a further object of the present invention to provide a process for preparing a *Clostridium perfringens* type A enterotoxin toxoid that is nontoxic to mammalian cells and that contains amino acids 171 through 319 of *Clostridium perfringens* type A enterotoxin.

It is a further object of this invention to demonstrate that the 30 carboxy-terminal terminal amino acids of *Clostridium perfringens* type A enterotoxin are sufficient for recognizing and irreversibly binding to the *Clostridium perfringens* type A enterotoxin receptor, and thus define these 30 carboxy-terminal amino acids as a functional receptor-binding domain.

These and other objects of the invention will be more fully understood from the following description of the invention and the claims appended hereto.

DESCRIPTION OF THE PREFERRED EMBODIMENTS

As used herein, the term "patient" includes members of the animal kingdom including but not limited to human beings.

The continuous *Escherichia coli* strains, recombinant toxoid producing plasmids and methods of preparing and using the strains and plasmids of this invention provide for the prophylaxis and treatment of the symptoms associated with food poisoning and other gastrointestinal illnesses in patients due to *Clostridium perfringens* type A enterotoxin.

The ability of bacterial toxins to kill or harm the cells of a patient is dependent upon the toxin's ability to specifically bind to membrane receptors on sensitive cells. Thus, binding to membrane receptors on mammalian cells is the obligatory first molecular event in the cytotoxic action of bacterial toxins. The present invention provides a recombinant DNA plasmid or bacteriophage transfer vector having an *Escherichia coli* expression vector and a DNA sequence encoding for a *Clostridium perfringens* type A enterotoxin gene fragment that produces a *Clostridium perfringens* type A enterotoxin receptor-binding region. This plasmid or bacteriophage includes a gene fragment having carboxy-terminal amino acids 171 through 319.

To determine directly which activities are associated with *Clostridium perfringens* type A enterotoxin, the 3' half of the enterotoxin gene was cloned and expressed in *Escherichia coli* in this invention. To further define the activities encoded by this *Clostridium perfringens* type A enterotoxin fragment, the 3' 90 nucleotides (encoding amino acids 290 through 319) of the *Clostridium perfringens* type A enterotoxin gene were subcloned and expressed in this invention. *Escherichia coli* lysates containing the resulting expressed gene fragments were tested for their ability to inhibit competitively the specific binding of wild type radioiodinated [$^{125}$I]-*Clostridium perfringens* type A enterotoxin to receptors and for their ability to react with *Clostridium perfringens* type A enterotoxin antibodies. *Clostridium perfringens* type A enterotoxin gene fragment encoding amino acids 171 through 319, and more specifically, *Clostridium perfringens* type A enterotoxin gene fragment encoding amino acids 290 through 319 were found to inhibit completely the specific-binding of [$^{125}$I]-*Clostridium perfringens* type A enterotoxin to receptors and to react with polyclonal *Clostridium perfringens* type A enterotoxin antibodies. Thus, this invention demonstrates that the receptor binding properties of *Clostridium perfringens* type A enterotoxin are located within the carboxy-terminal amino acids of *Clostridium perfringens* type A enterotoxin and more specifically, within the 30 carboxy-terminal amino acids of *Clostridium perfringens* type A enterotoxin.

The present invention provides a continuous *Escherichia coli* strain that produces a recombinant *Clostridium perfringens* type A enterotoxin toxoid comprising a *Clostridium perfringens* enterotoxin gene fragment encoding amino acids 171 through 319 subcloned into an *Escherichia coli* expression vector for forming a plasmid containing the *Escherichia coli* expression vector and the *Clostridium perfringens* type A enterotoxin gene fragment wherein the plasmid is capable of producing the toxoid. More specifically, the present invention provides a continuous *Escherichia coli* strain that produces a recombinant *Clostridium perfringens* type A enterotoxin toxoid having a *Clostridium perfringens* type A enterotoxin gene fragment encoding amino acids 290 through 319 subcloned into an *Escherichia coli* expression vector for forming a plasmid containing the *Escherichia coli* expression vector and the *Clostridium perfringens* type A enterotoxin gene fragment wherein the plasmid is capable of producing the toxoid.

The present invention provides for a process for preparing a toxoid producing plasmid including generating a recombinant *Clostridium perfringens* enterotoxin DNA expression library, screening the library with antibodies to *Clostridium perfringens* enterotoxin to obtain a positive-scoring plaque, and subcloning the positive scoring plaque into an expression vector to obtain a toxoid producing plasmid containing a *Clostridium perfringens* type A enterotoxin gene fragment encoding the carboxy-terminal amino acids.

In the process for preparing a toxoid producing plasmid of this invention, *Clostridium perfringens* NCTC 8239, which is a high producer of *Clostridium perfringens* type A enterotoxin, was used as the DNA source for library construction. *Escherichia coli* Y1089 and Y1090, λgt11 DNA and bacteriophage packaging reagents, *Escherichia coli* HB101, and plasmid pGEM4, were purchased from Promega Biotech. Expression plasmid pEV-vrf1, EcoRI and *Escherichia coli* RR1 (pRK248cIts) were obtained from Hoffmann-La Roche Inc.

More specifically, the process of this invention includes isolating DNA from *Clostridium perfringens* by the method of Marmur [J. Marmur, "A procedure for the isolation of deoxyribonucleic acid from microorganisms," *J. Mol. Bio.*, 3:208–218 (1961)], generating a recombinant λgt11 library by random shearing of DNA through a needle, blunting of the ends, protecting of endogenous EcoRI sites, adding of EcoRI linkers, activating the ends with EcoRI, and ligating to phage arms, all of which are well known to those persons skilled in the art. Screening of recombinant λgt11 plaques was performed by immunoblotting. The primary antiserum used was an anti-*Clostridium perfringens* type A enterotoxin monoclonal antibody MAb3C9.

When the λgt11 library of *Clostridium perfringens* DNA was screened with anti-*Clostridium perfringens* type A enterotoxin MAb3C9, one positive-scoring plaque was obtained and named lambda ph161 (λph161). The construction of the λgt11 library and the resultant λph161 is set forth in FIG. 1. Since it is known that MAb3C9 recognizes an epitope which appears to be at or near the receptor-binding domain of *Clostridium perfringens* type A enterotoxin, this suggests that the positive scoring plaque λph161 contains a *Clostridium perfringens* type A enterotoxin gene insert that encodes a *Clostridium perfringens* type A enterotoxin receptor-binding domain. Lambda ph161 was isolated and used to generate a temperature sensitive ($t^s$) lysogen in *Escherichia coli* Y1089 for phage storage.

The process of this invention includes subcloning lambda ph161 DNA into the *Escherichia coli* expression vector pEV-vrf1 to obtain a toxoid producing plasmid pPH300, as set forth in FIG. 1.

Figure 2:
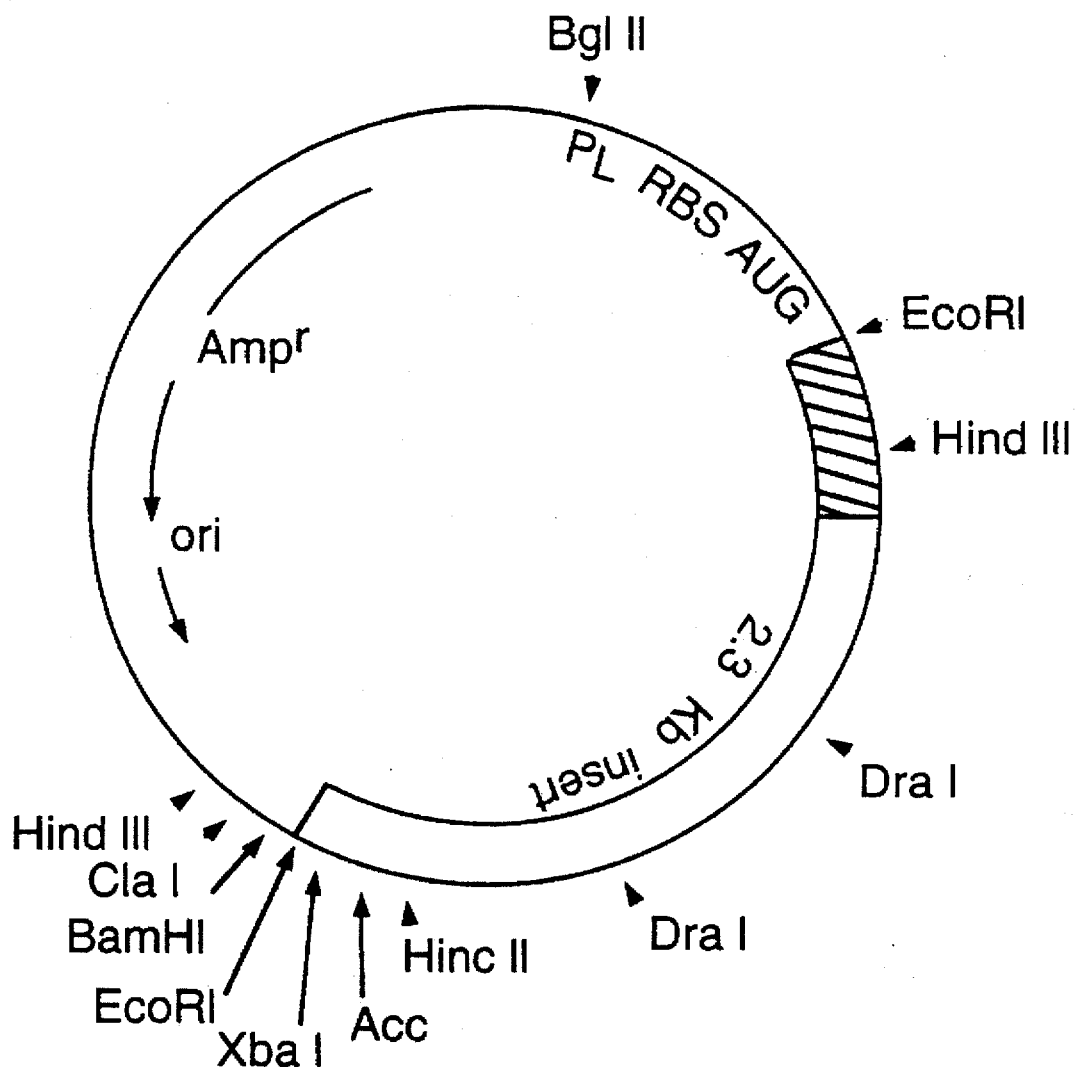
FIG. 2 shows a restriction endonuclease cleavage map for plasmid pPH300.
Figure 3:
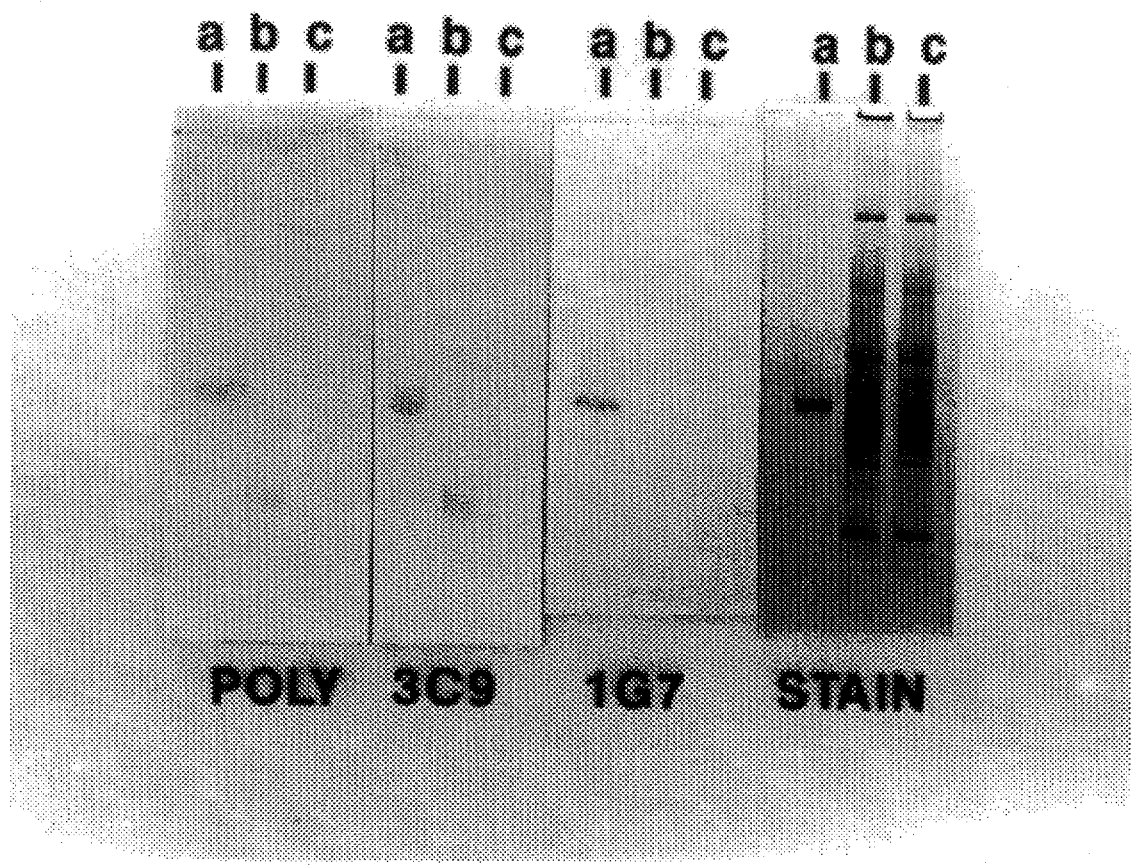
FIG. 3 shows the results of immunoblotting *Clostridium perfringens* type A enterotoxin, a lysate of *Escherichia coli* containing *Clostridium perfringens* type A enterotoxin gene fragment encoding amino acids 171-319 (pPH300) and a negative control *Escherichia coli* lysate (pEV-vrf1).

FIG. 2 shows the restriction endonuclease cleavage map for plasmid pPH300. Following induction, lysates from *Escherichia coli* containing pPH300 (expressing the *Clostridium perfringens* type A enterotoxin fragment of amino acids 171 through 319) and pEV-vrf1 (negative control) were immunoblotted. The results of the immunoblotting are set forth in FIG. 3. FIG. 3 shows that intact *Clostridium perfringens* type A enterotoxin (lanes a) reacted with all *Clostridium perfringens* type A enterotoxin antibodies. *Escherichia coli* lysates containing the *Clostridium perfringens* type A enterotoxin fragment encoding amino acids 171 through 319 (lanes b) reacted as a single band with polyclonal anti-*Clostridium perfringens* type A enterotoxin and with MAb3C9, but did not react with MAb1G7. MAb3C9 neutralizes *Clostridium perfringens* type A enterotoxin binding to its receptor, while MAb167 reacts with *Clostridium perfringens* type A enterotoxin but does not neutralize *Clostridium perfringens* type A enterotoxin action or affect *Clostridium perfringens* type A enterotoxin binding. Negative control *Escherichia coli* lysates (lanes c) showed no immunoreactivity with any *Clostridium perfringens* type A enterotoxin antibodies.

To identify which portion of the *Clostridium perfringens* type A enterotoxin gene had been cloned, DNA sequencing was performed on the 200-base-pair SmaI-HindIII *Clostridium perfringens* type A enterotoxin gene insert contained on plasmid pPH200 of FIG. 1. Both strands of this 200-base-pair insert were completely sequenced by the dideoxy method and deductively translated using techniques known by those persons skilled in the art. FIG. 4 shows the DNA sequence (top line of each horizontal row) and the derived amino acid sequence (bottom line of each horizontal row) from the *Clostridium perfringens* type A enterotoxin gene fragment encoding amino acids 171 through 319, SEQ ID NO:1. The results indicate that this invention has cloned the 3' half of the *Clostridium perfringens* type A enterotoxin gene and downstream regions.

The availability of a clone that expresses only the carboxy-terminal half of *Clostridium perfringens* type A enterotoxin permitted investigation of possible activities which may be associated with this region of the *Clostridium perfringens* type A enterotoxin molecule. Experiments were performed to examine whether *Clostridium perfringens* type A enterotoxin fragment of amino acids 171 through 319 recognizes *Clostridium perfringens* type A enterotoxin receptors on rabbit intestinal brush border membranes, the physiologic site of *Clostridium perfringens* type A enterotoxin action.

Figure 5:
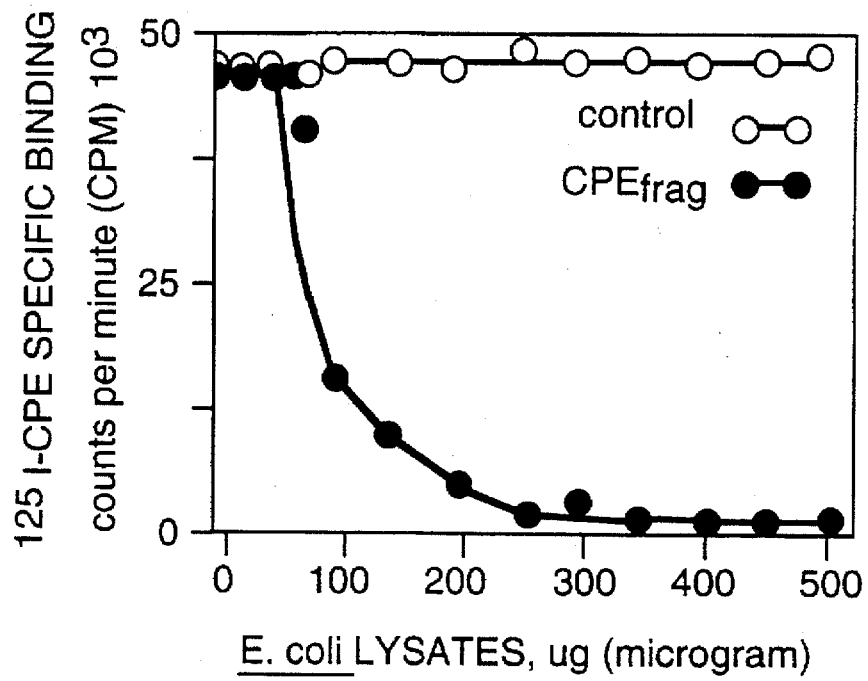
FIG. 5 shows competitive inhibition of radioiodinated [$^{125}$I]-*Clostridium perfringens* type A enterotoxin ($^{125}$I-CPE) specific binding to intestinal brush border membranes by lysates from *Escherichia coli* (*E. coli*) containing *Clostridium perfringens* type A enterotoxin gene fragment (CPE-frag) encoding amino acids 171-319.

*Escherichia coli* lysates producing *Clostridium perfringens* type A enterotoxin fragment corresponding to amino acids 171 through 319 were shown to competitively inhibit radioiodinated [$^{125}$I]-*Clostridium perfringens* type A enterotoxin specific binding to brush border membrane receptors in a dose-dependent manner as set forth in FIG. 5.

Figure 6:
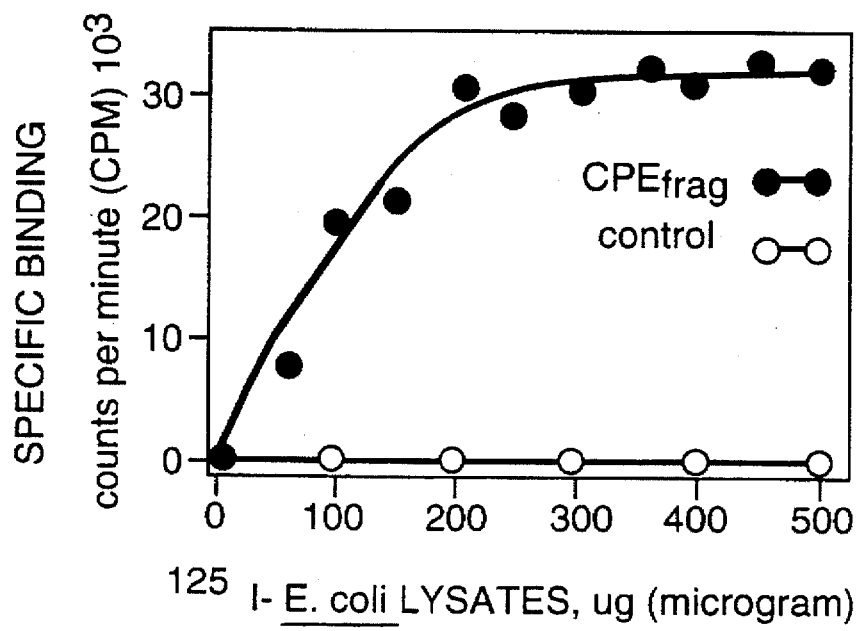
FIG. 6 shows specific binding of radioiodinated [$^{125}$I]-labeled lysates to brush border membranes.

To demonstrate that lysates containing *Clostridium perfringens* type A enterotoxin fragment corresponding to amino acids 171 through 319 contain an agent which specifically binds to brush border membranes, *Escherichia coli* lysates containing *Clostridium perfringens* type A enterotoxin fragment corresponding to amino acids 171 through 319 and negative control *Escherichia coli* lysates were radioiodinated. In this invention, the [$^{125}$I]-labeled lysates of *Clostridium perfringens* type A entertoxin fragment corresponding to amino acids 171 through 319 were found to bind specifically to brush border membranes in a saturable manner as shown in FIG. 6. This binding is due to *Clostridium perfringens* type A enterotoxin fragment corresponding to amino acids 171 through 319 in lysates, since no specific binding was detected with negative control $^{125}$I-labeled lysates.

Additional preincubation competitive-binding studies were performed to demonstrate further that *Clostridium perfringens* type A enterotoxin fragment corresponding to amino acids 171 through 319 and *Clostridium perfringens* type A enterotoxin compete for the same brush border membrane receptors and that *Clostridium perfringens* type A enterotoxin fragment containing amino acids 171 through 319 is the active agent in those lysates. The results of these studies are set forth in FIG. 7. FIGS. 7A and 7B confirm that specific binding of [$^{125}$I]-*Clostridium perfringens* type A enterotoxin or [$^{125}$I]-*Clostridium perfringens* type A enterotoxin fragment corresponding to amino acids 171 through 319 lysate can be specifically inhibited by either unlabeled *Clostridium perfringens* type A enterotoxin lysate or unlabeled *Clostridium perfringens* type A enterotoxin fragment corresponding to amino acids 171 through 319 lysate but not by control lysates. FIGS. 7A and 7B also show that preincubation of either unlabeled *Clostridium perfringens* type A enterotoxin lysate or *Clostridium perfringens* type A enterotoxin fragment corresponding amino acids 171 through 319 lysate with MAb3C9 eliminated their subsequent abilities to compete successfully against [$^{125}$I]-*Clostridium perfringens* type A enterotoxin or [$^{125}$I]-labeled *Clostridium perfringens* type A enterotoxin fragment corresponding to amino acids 171 through 319 lysate binding. However, preincubation of these unlabeled competitors with MAb1G7 did not affect their subsequent abilities to compete against [$^{125}$I]-*Clostridium perfringens* type A enterotoxin lysate or [$^{125}$I]-labeled *Clostridium perfringens* type A enterotoxin fragment corresponding to amino acids 171 through 319 lysate binding. This specific neutralization of binding competition by MAb3C9 shown in FIGS. 7A and 7B indicates that *Clostridium perfringens* type A enterotoxin fragment corresponding to amino acids 171 through 319 of the enterotoxin is the active binding competitor in the lysates.

Results shown in FIG. 7C support that *Clostridium perfringens* type A enterotoxin fragment corresponding to amino acids 171 through 319 of the enterotoxin specifically recognize *Clostridium perfringens* type A enterotoxin receptors. Since it is known that *Clostridium perfringens* type A enterotoxin and cholera toxin (CT) recognize different brush border membrane receptors, lysates containing *Clostridium*

*perfringens* type A enterotoxin fragment corresponding to amino acids 171 through 319 of the enterotoxin should not compete with radioiodinated [$^{125}$I]-cholera toxin binding if this *Clostridium perfringens* type A enterotoxin fragment is specific for *Clostridium perfringens* type A enterotoxin receptors. As set forth in FIG. 7C, neither unlabeled *Clostridium perfringens* type A enterotoxin fragment corresponding to amino acids 171 through 319 of the enterotoxin nor negative control lysates significantly competed for [$^{125}$I]-cholera toxin-specific binding sites. Conversely, unlabeled cholera toxin did not affect either [$^{125}$I]-*Clostridium perfringens* type A enterotoxin or [$^{125}$I]-labeled *Clostridium perfringens* type A enterotoxin fragment corresponding to amino acids 171 through 319 lysate binding as shown in FIGS. 7A and 7B.

When $^3$H-labeled nucleotide release from Vero (African green monkey kidney) cells was used to test for *Clostridium perfringens* type A enterotoxin cytotoxicity, no cytotoxic effects were detected with lysates containing *Clostridium perfringens* type A enterotoxin fragment corresponding to amino acids 171 through 319 of the enterotoxin, even up to 25 mg of protein (containing 2,500 pmol of the *Clostridium perfringens* type A enterotoxin fragment corresponding to amino acids 171 through 319) per well. However, 5 µg ($\cong$135 pmol) of purified *Clostridium perfringens* type A enterotoxin per well caused significant $^3$H-labeled nucleotide release from Vero cells, as set forth in FIG. 8.

Figure 8:
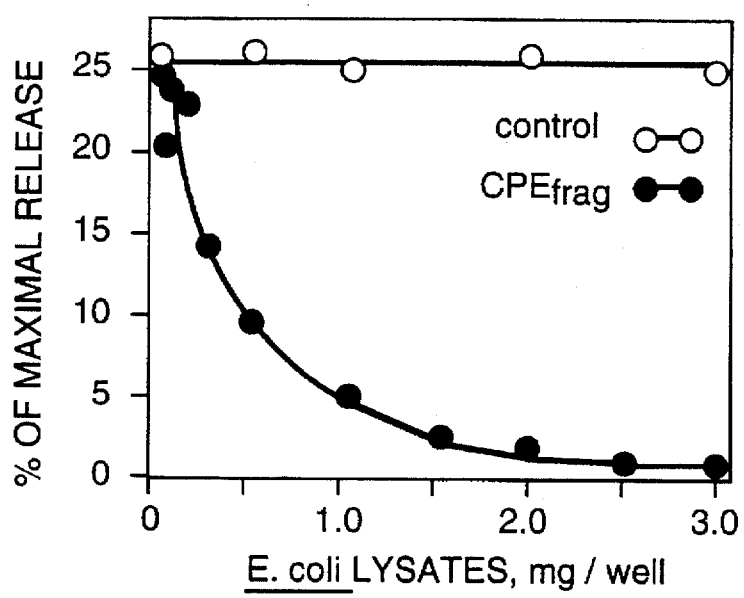
FIG. 8 shows protection of Vero cells from *Clostridium perfringens* type A enterotoxin induced cytotoxicity by preincubation with lysates of *Clostridium perfringens* type A enterotoxin fragment (CPE-frag) containing amino acids 171-319.

The results shown in FIG. 8 demonstrate the specificity of *Clostridium perfringens* type A enterotoxin fragment corresponding to amino acids 171 through 319 for the physiologic receptor on Vero cells which mediates *Clostridium perfringens* type A enterotoxin cytotoxicity. Preincubation of Vero cells with *Clostridium perfringens* type A enterotoxin fragment of amino acids 171 through 319 lysates protected these cells from subsequent *Clostridium perfringens* type A enterotoxin challenge in a dose-dependent manner. The protection was essentially complete at 2 to 3 mg protein of lysates containing *Clostridium perfringens* type A enterotoxin fragment corresponding to amino acids 171 through 319 per well. Negative control lysates had no protective effect at 3 mg of protein per well. FIG. 8 demonstrates that the *Clostridium perfringens* type A enterotoxin toxoid containing the fragment corresponding to amino acids 171–319 is nontoxic to mammalian cells, and that preincubation of Vero cells with increasing amounts of this toxoid protects these cells from damage due to subsequent exposure to *Clostridium perfringens* type A enterotoxin.

Additionally, MAb3C9 pretreatment of *Clostridium perfringens* type A enterotoxin fragment corresponding to amino acids 171 through 319 lysates specifically eliminated the subsequent ability of these lysates to protect Vero cells, while pretreatment of *Clostridium perfringens* type A enterotoxin fragment corresponding to amino acids 171 through 319 lysates with MAb1G7 did not have this effect.

In another embodiment of this invention, a continuous *Escherichia coli* strain is provided that produces a recombinant *Clostridium perfringens* type A enterotoxin toxoid that may be used as a vaccine or as a therapeutic agent. This toxoid is produced from the insertion of a *Clostridium perfringens* type A enterotoxin fragment encoding amino acids 171 through 319 into an *Escherichia coli* expression vector to form a plasmid. This plasmid contains the *Escherichia coli* expression vector and the *Clostridium perfringens* type A enterotoxin gene fragment. In *Escherichia coli*, this plasmid is capable of producing the vaccine. This vaccine may be incorporated in a suitable pharmaceutical carrier and administered in an effective dose to a patient as a prophylactic measure to prevent food poisoning due to *Clostridium perfringens* type A enterotoxin. This toxoid may be incorporated into a suitable pharmaceutical carrier and administered to a patient in a therapeutically effective dose for treating the symptoms associated with food poisoning due to *Clostridium perfringens* type A enterotoxin. More specifically, the *Escherichia coli* expression vector of this embodiment is pEV-vrf1 and the plasmid of this embodiment is plasmid pPH300.

Figure 9:
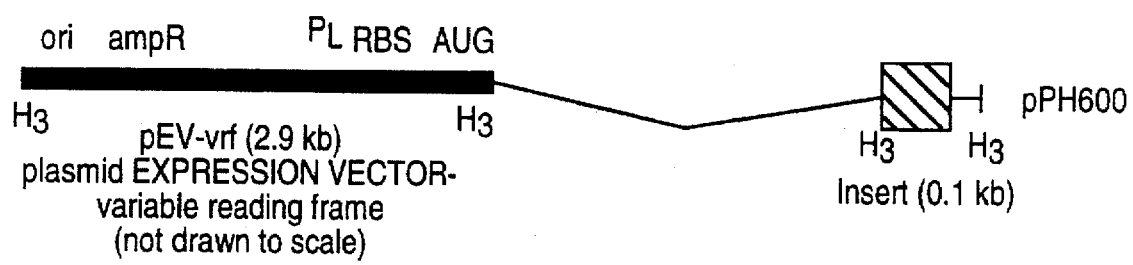
FIG. 9 shows a restriction endonuclease cleavage map for plasmid pPH600.

In another embodiment of this invention, a continuous *Escherichia coli* cell line is provided for that produces a recombinant *Clostridium perfringens* type A enterotoxin toxoid from a *Clostridium perfringens* type A enterotoxin gene fragment encoding amino acids 290 through 319 subcloned into an *Escherichia coli* expression vector for forming a plasmid designated pPH600. This *Escherichia coli* expression vector includes pEV-vrf3. FIG. 9 shows the restriction endonuclease cleavage map for plasmid pPH600. This plasmid contains the *Escherichia coli* expression vector and the *Clostridium perfringens* type A enterotoxin gene fragment encoding amino acids 290 through 319 and is capable of producing the toxoid. This toxoid recognizes, irreversibly binds to and saturates receptor sites on intestinal membranes, and thus effectively competes for these sites with *Clostridium perfringens* type A enterotoxin. This toxoid is nontoxic to mammalian cells. This toxoid may be used in patients as a therapeutic agent for the treatment of the symptoms associated with food poisoning due to *Clostridium perfringens* enterotoxin. More specifically, this toxoid may be incorporated into a suitable pharmaceutical carrier and administered to a patient in a therapeutically effective dose for treating the symptoms associated with food poisoning due to *Clostridium perfringens* type A enterotoxin. This toxoid may be used as a vaccine in patients for the prophylaxis of the symptoms associated with food poisoning due to *Clostridium perfringens* type A enterotoxin. More specifically, this vaccine may be incorporated in a suitable pharmaceutical carrier and administered in a prophylactically effective dose to a patient as a measure to prevent food poisoning due to *Clostridium perfringens* type A enterotoxin.

This invention provides a process for preparing plasmid pPH600 that contains an *Escherichia coli* expression vector and a *Clostridium perfringens* type A enterotoxin gene fragment encoding amino acids 290 through 319. The construction of plasmid pPH600 is shown in FIG. 10. This process includes digesting the DNA of plasmid pPH300 with Hind III (*Haemophilus influenzae* R$_d$) to completion, separating the digested DNA on agarose gel, isolating a kilobase insert band of DNA, and ligating the 0.1 kilobase insert band of DNA into the Hind III site of plasmid pEV-vrf3 to yield plasmid pPH600.

In the process for preparing plasmid pPH600, *Escherichia coli* RRI (pRK248cIts) and inducible expression vector-variable reading frame plasmid (pEV-vrf3) were employed, and were obtained from Hoffmann-LaRoche Inc. These vectors contain an inducible lambda promoter, ribosome binding site and AUG start codon just upstream of a multiple cloning site. The parent plasmid plasmid pPH300, was isolated, digested with appropriate restriction enzymes and dephosphorylated by standard techniques, all well known to those persons skilled in the art.

More specifically, this process includes isolating the *Clostridium perfringens* type A enterotoxin gene insert for plasmid pPH600 by digesting plasmid pPH300 that contains the 3' half of the *Clostridium perfringens* type A enterotoxin gene with restriction enzymes EcoRI (*Escherichia coli*

RY13) and Hind III (1 to 3 units of enzyme/ug plasmid DNA) in supplied buffer for 1 hour at 37° C. (Centigrade), terminating the disections by extracting twice with an equal volume of phenol followed by two extractions with a chloroform to isoamyl alcohol mixture in the ratio of 24:1, adding ammonium acetate to a final concentration of 2.5M (molar), precipitating the DNA by adding two volumes of 95 percent ethanol with incubation at −80° C. for 15 minutes to form DNA pellets, suspending and resolving the DNA pellets on a 4 percent low melting agarose gel using a HpaII (*Haemophilus parainfluenzae*) digest of pBR322 as a molecular size marker, visualizing DNA insert bands by staining the gel with ethidium bromide, excising a 0.1 Kb band to form a gel slice, melting the gel slices at 60° C., diluting the gel slices with deionized water at a ratio of 1:5 (gel slices:deionized water), adding the gel slices to digested dephosphorylated vector DNA at a ratio of 4:1 (insert:vector), incubating the insert and the vector DNA overnight at 24° C. with 1 unit of $T_4$ DNA ligase in the supplied ligase buffer, remelting the ligation mixes, transforming competent *Escherichia coli* RR1 by the standard method using $CaCl_2$, plating the *Escherichia coli* RR1 on Luria-Bertani plates, screening colonies containing 100 ug/ml ampicillin for the plasmid pPH600 construct by preparing miniplasmid DNA and subsequent restriction mapping using standard techniques well known by those persons skilled in the art. The identity of the *Clostridium perfringens* type A enterotoxin gene insert in plasmid pPH600 was further confirmed by DNA sequencing using standard techniques well known to those persons skilled in the art.

It will be appreciated by those persons skilled in the art that this invention provides for a continuous *Escherichia coli* strain that produces a recombinant *Clostridium perfringens* type A enterotoxin toxoid that may be used as a vaccine or as a therapeutic agent. It will be understood by those persons skilled in the art that this toxoid is produced from the insertion of a *Clostridium perfringens* type A enterotoxin gene fragment encoding amino acids 290 through 319 into an *Escherichia coli* expression vector that includes pEV-vrf3 to form plasmid pPH600. This plasmid contains the *Escherichia coli* expression vector and the *Clostridium perfringens* type A enterotoxin gene fragment encoding amino acids 290 through 319.

Figure 11:
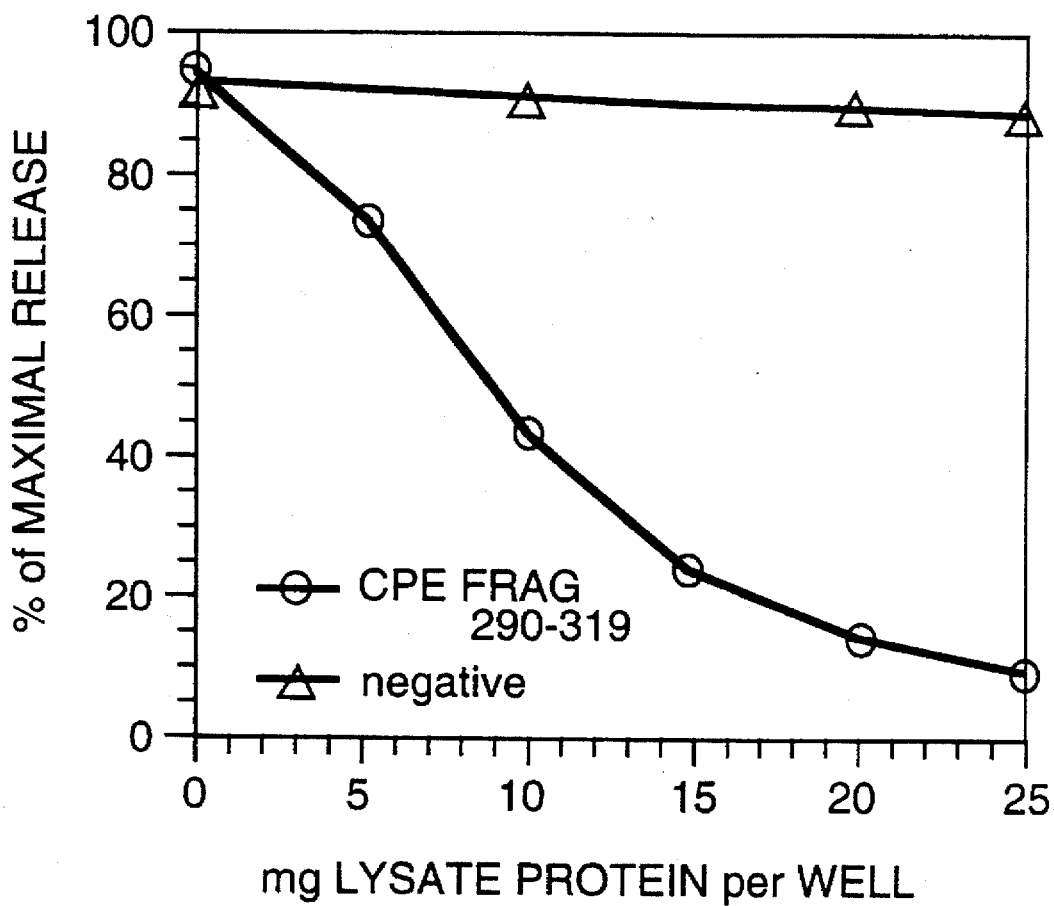
FIG. 11 shows Vero cell protection assays that indicate *Clostridium perfringens* type A enterotoxin fragment containing amino acids 290-319 (CPE FRAG 290-319) has functional *Clostridium perfringens* type A enterotoxin-like binding activity.

To confirm that *Clostridium perfringens* type A enterotoxin fragment corresponding to amino acids 290 through 319 effectively competes for the physiologic *Clostridium perfringens* type A enterotoxin receptor which mediates cytotoxicity, Vero cell protection experiments were performed. FIG. 11 sets forth the results of these protection assays. FIG. 11 indicates that preincubation with increasing concentrations of lysates containing *Clostridium perfringens* type A entertoxin fragment corresponding to amino acids 290 through 319 protects Vero cells from subsequent challenge with *Clostridium perfringens* type A enterotoxin. Preincubation of Vero cells with negative control lysates did not affect subsequent *Clostridium perfringens* type A enterotoxin cytotoxicity. These results indicate that *Clostridium perfringens* type A enterotoxin fragment corresponding to amino acids 290 through 319 has functional *Clostridium perfringens* type A enterotoxin-like binding activity.

Figure 12:
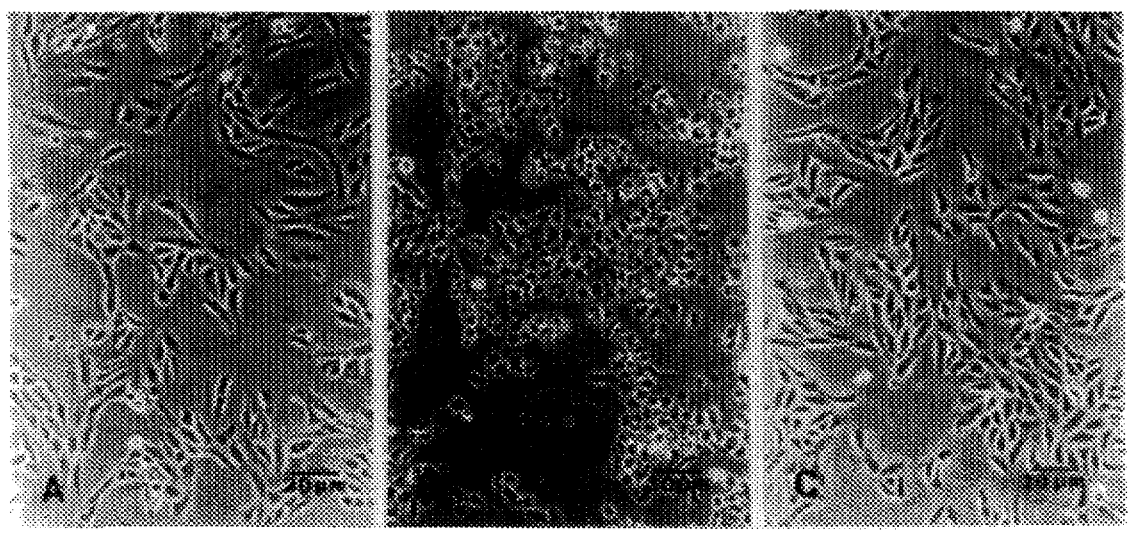
FIG. 12 shows: (A) normal Vero cells; (B) morphologic damage of Vero cells due to challenge with *Clostridium perfringens* type A enterotoxin; and (C) Vero cells challenged with *Clostridium perfringens* enterotoxin fragment containing amino acids 171–319.

Changes in Vero cell shape ("rounding up") and formation of membrane lesions ("blebs") were observed using direct phase contrast microscopic visualization thirty (30) minutes after Vero cells were challenged with either *Clostridium perfringens perfringens* type A enterotoxin or *Clostridium perfringens* type A enterotoxin fragment corresponding to amino acids 171 through 319 at 37° Centigrade. FIG. 12A–C sets forth the gross changes in Vero cellular morphology. FIG. 12A depicts normal Vero cells that are spindle shaped. FIG. 12B shows the morphologic damage that occurs when a normal Vero cell is challenged with *Clostridium perfringens* type A enterotoxin. *Clostridium perfringens* type A enterotoxin causes normal spindle shaped Vero cells to become round in appearance and to form membrane lesions leading to lysis. FIG. 12C shows that normal Vero cells challenged with *Clostridium perfringens* type A enterotoxin fragment of amino acids 171 through 319 undergo substantially no morphological changes.

Another embodiment of this invention provides for a synthetic peptide. This synthetic peptide was based on the translated DNA sequence of plasmid pPH600 encoding *Clostridium perfringens* type A enterotoxin fragment corresponding to amino acids 290 through 319. The amino acid composition of this synthetic peptide was confirmed by amino acid composition analysis well known to those persons skilled in the art. The amino acid sequence of this synthetic peptide, SEQ ID NO:3, is shown in FIG. 13. The synthetic peptide is substantially identical to the *Clostridium perfringens* type A enterotoxin fragment corresponding to amino acids 290 through 319. For conjugating the peptide to a protein carrier for immunization studies, a cysteine also was added to the N-terminus of some of the synthetic peptide. In order to render this cysteine containing synthetic peptide immunogenic, it was coupled to thyroglobulin through the sulfhydral group of the N-terminal cysteine using the chemical crosslinker m-maleimidobenzoyl-N-hydroxysuccinimide ester.

This synthetic peptide was purified to homogeneity by reverse phase high performance liquid chromatography. A negative control peptide was designed containing the amino acid sequence ASN THR ASP GLY SER THR ASP TYR GLY ILE LEU $NH_2$ GLN ILE ASP SER ARG COOH.

Figure 14:
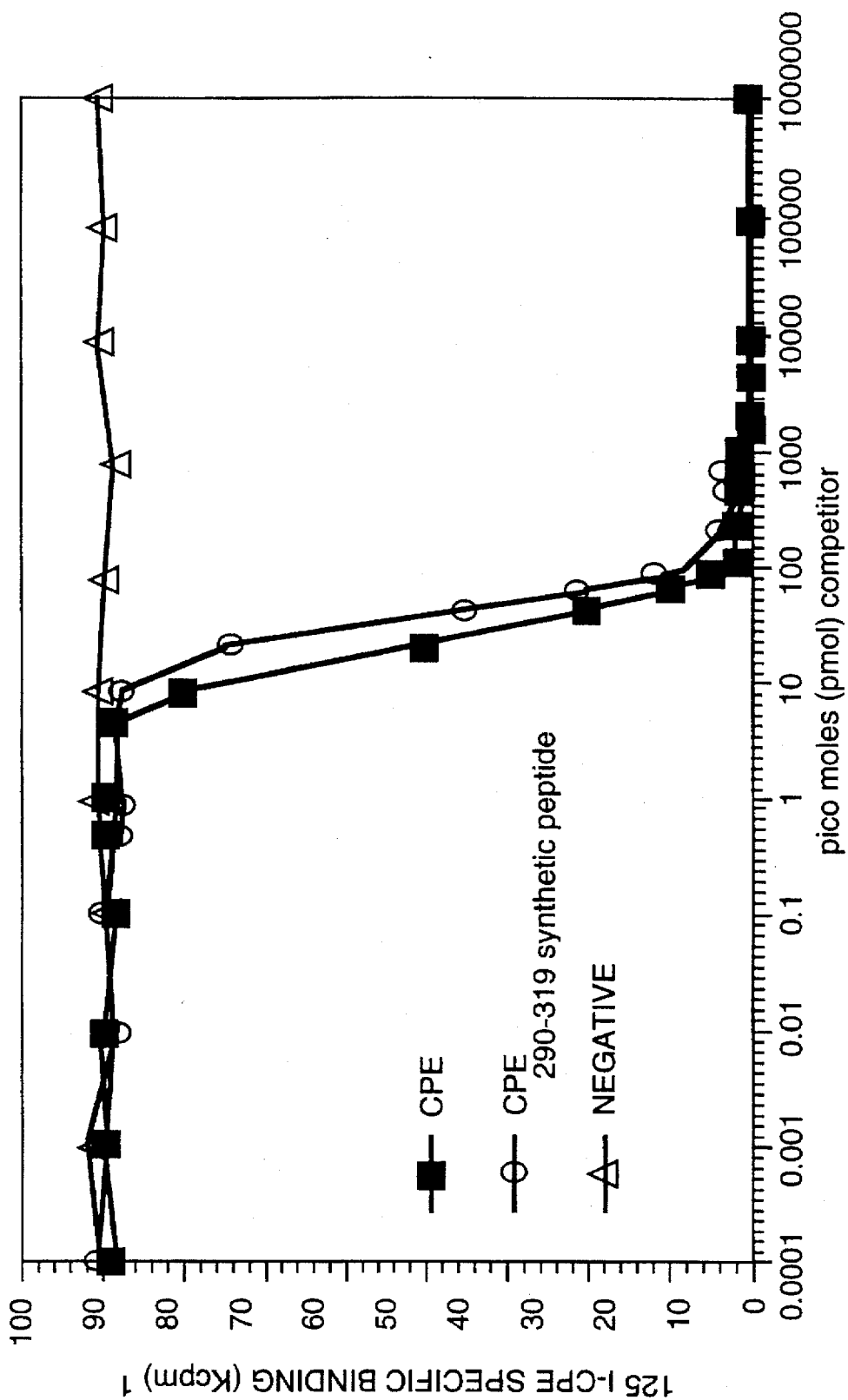
FIG. 14 shows that the *Clostridium perfringens* type A enterotoxin fragment synthetic peptide corresponding to amino acids 290 through 319 (CPE 290–319 synthetic peptide) inhibits the binding of radioiodinated [$^{125}$I]-*Clostridium perfringens* type A enterotoxin to brush border membrane receptors.

To demonstrate that the *Clostridium perfringens* type A enterotoxin fragment synthetic peptide corresponding to amino acids 290 through 319 inhibits the binding of radioiodinated [$^{125}$I]-*Clostridium perfringens* type A enterotoxin to brush border membrane receptors, increasing amounts of unlabelled *Clostridium perfringens* type A enterotoxin or synthetic peptide were preincubated for fifteen minutes with brush border membranes (100 ug of protein), radioiodinated [$^{125}$I]-*Clostridium perfringens* type A enterotoxin was added, and the brush border membranes were assayed. The results of this study, as shown in FIG. 14, indicate that both *Clostridium perfringens* type A enterotoxin (CPE) and *Clostridium perfringens* type A enterotoxin fragment synthetic peptide corresponding to amino acids 290–319 (CPE 290–319 synthetic peptide) reduce subsequent [$^{125}$I]-*Clostridium perfringens* type A enterotoxin specific binding in a dose-response manner. FIG. 14 also shows that the negative control peptide (negative) does not affect [$^{125}$I]-*Clostridium perfringens* type A enterotoxin binding even at high concentrations.

Figure 15:
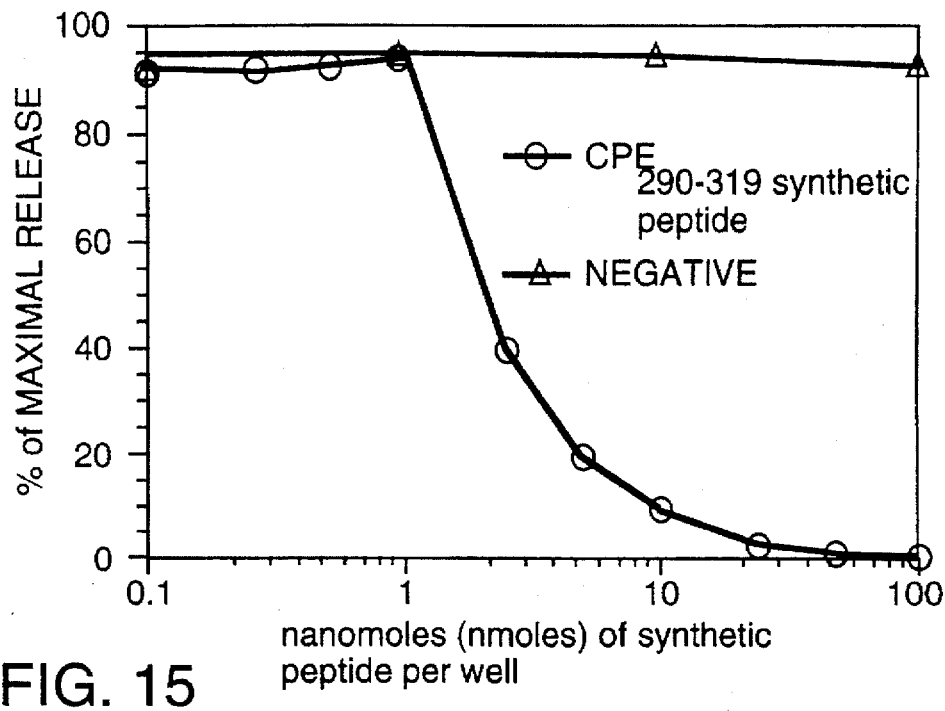
FIG. 15 shows that the *Clostridium perfringens* type A enterotoxin fragment synthetic peptide corresponding to amino acids 290 through 319 recognizes and binds to the *Clostridium perfringens* enterotoxin receptor that mediates cytotoxicity.

To demonstrate that the *Clostridium perfringens* type A enterotoxin fragment synthetic peptide corresponding to amino acids 290 through 319 recognizes and binds to the *Clostridium perfringens* enterotoxin receptor that mediates cytotoxicity, radiolabelled rubidium ($^{86}$Rb-labelled) Vero cells were preincubated with increasing amounts of the synthetic peptide, washed twice with 0.32 molar sucrose containing 10 millimoles of HBSS (Hank's balanced salt solution) ph7.4, and challenged with *Clostridium perfringens* type A enterotoxin. FIG. 15 shows the nanomoles (nmoles) of synthetic peptide per well plotted against percent of maximal release of label from the Vero cells. The results shown in FIG. 15 indicate that Vero cells are protected from Clostridium perfringens enterotoxin challenge by preincubation with Clostridium perfringens type A enterotoxin fragment synthetic peptide containing amino acids 290 through 319 (CPE 290–319 synthetic peptide) but not by preincubation with the negative control peptide (negative). From FIG. 15, it will be appreciated that this protection occurs in a dose-response manner and complete protection for approximately $10^6$ cells requires about 50 to about 100 nanomoles of synthetic peptide.

Figure 16:
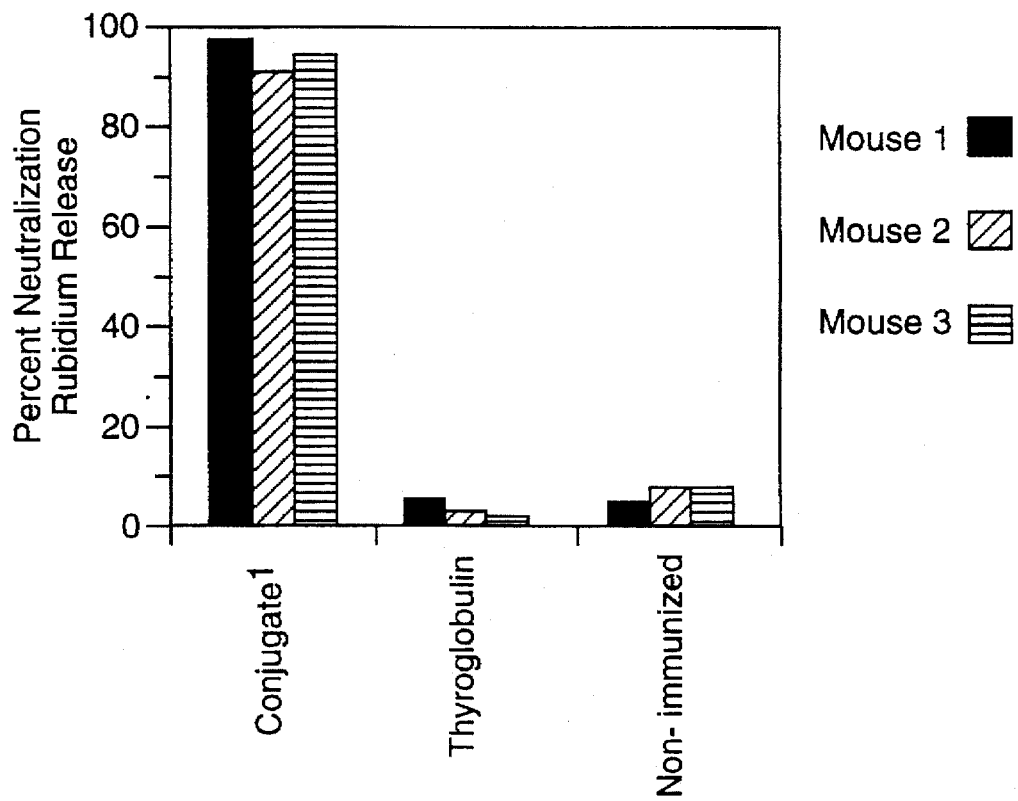
FIG. 16 shows that mice immunized with synthetic peptide conjugated to thyroglobulin neutralized rubidium release indicating that the synthetic peptide conjugate neutralized *Clostridium perfringens* enterotoxin activity.

In another experiment, three groups of mice were immunized with either synthetic peptide conjugated to thyroglobulin (conjugate), thyroglobulin alone or no immunogen (non-immunized). Sera harvested from each of these mice were examined for their ability to inhibit the rubidium release caused by treatment of vero cells with Clostridium perfringens type A enterotoxin. FIG. 16 shows the data expressed as a percentage of the total cell-associated rubidium remaining after treatment of cells with Clostridium perfringens enterotoxin and sera. All three sera obtained from mice immunized with the synthetic peptide conjugate neutralized rubidium release indicating that the synthetic peptide conjugate neutralized Clostridium perfringens enterotoxin activity. The results of these experiments demonstrate that purified Clostridium perfringens type A enterotoxin fragment synthetic peptide containing amino acids 290 through 319 retains Clostridium perfringens enterotoxin-like binding activity and elicits the production of neutralizing antibodies essential for vaccine effectiveness.

It will be appreciated by those persons skilled in the art that this invention provides a process for the cloning of the 3' half of the Clostridium perfringens type A enterotoxin gene with an Escherichia coli expression vector using recombinant techniques to allow for the production of vaccine producing plasmids. These plasmids are capable of producing Clostridium perfringens type A enterotoxin toxoids that are nontoxic to mammalian cells and that contain a Clostridium perfringens type A enterotoxin fragment that recognizes, irreversibly binds to and saturates receptor sites on intestinal membranes, thus, competing for these sites with Clostridium perfringens type A enterotoxin. It will be understood that the Clostridium perfringens type A enterotoxin fragment amino acids of this invention are amino acids 171 through 319, and more specifically amino acids 290 through 319.

It will be appreciated by those persons skilled in the art that this invention provides for a Clostridium perfringens type A enterotoxin toxoid having an expression vector and a Clostridium perfringens type A enterotoxin gene fragment of amino acids 290 through 319 that is capable of preventing or treating the symptoms associated with Clostridium perfringens food poisoning in patients.

Whereas particular embodiments of this invention have been described above for purposes of illustration, it will be evident to those persons skilled in the art that numerous variations of the details of the present invention may be made without departing from the invention as defined in the appended claims that follow the SEQUENCE LISTING.

What is claimed:

1. An isolated DNA molecule consisting of a nucleotide sequence which encodes a carboxy-terminal protein fragment of the *Clostridium perfringens* type A enterotoxin protein consisting of amino acid 171 to amino acid 319 of said *Clostridium perfringens* type A enterotoxin protein.

2. A bacteriophage vector comprising said isolated DNA molecule of claim 1.

3. A DNA plasmid vector molecule comprising said isolated DNA molecule of claim 1.

4. A microorganism transformed by said DNA plasmid vector molecule of claim 3.

5. The microorganism of claim 4 which is *Escherichia coli*.

6. The isolated DNA molecule of claim 1 wherein said resulting carboxy-terminal protein fragment is SEQ ID NO:1.

7. A bacteriophage vector comprising said DNA molecule of claim 6.

8. A DNA plasmid vector molecule comprising said isolated DNA molecule of claim 6.

9. An isolated DNA molecule consisting of a nucleotide sequence which encodes a carboxy-terminal protein fragment of the *Clostridium perfringens* type A enterotoxin protein consisting of amino acid 291 to amino acid 319 of said *Clostridium perfringens* type A enterotoxin protein.

10. A bacteriophage vector comprising said isolated DNA molecule of claim 9.

11. A DNA vector molecule comprising said isolated DNA molecule of claim 9.

12. A microorganism transformed by said DNA plasmid vector molecule of claim 11.

13. The microorganism of claim 12 which is *Escherichia coli*.

14. The nucleic acid sequence of claim 9 wherein the expressed protein fragment is SEQ ID NO:3.

15. A DNA plasmid vector molecule which comprises said DNA molecule of claim 14.

* * * * *

UNITED STATES PATENT AND TRADEMARK OFFICE
CERTIFICATE OF CORRECTION

PATENT NO. : 5,695,956
DATED : December 9, 1997
INVENTOR(S) : BRUCE A. MC CLANE, PHILIP C. HANNA and TIMOTHY A. MIETZNER It is certified that error appears in the above-identified patent and that said Letters Patent is hereby corrected as shown below:

Column 12, line 49, "a" should be --a 0.1--.

Signed and Sealed this

Twentieth Day of July, 1999

Attest:

Q. TODD DICKINSON

*Attesting Officer*     Acting Commissioner of Patents and Trademarks

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 450 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( A ) ORGANISM: Clostridium perfringens
        ( B ) STRAIN: NCTC 8239

( i x ) FEATURE:
        ( A ) NAME/KEY: CDS
        ( B ) LOCATION: 1..450

( x i ) SEQUENCE DESCRIPTION: SEQ ID NO:1:

```
TTA  GGA  AAT  ATT  GAT  CAA  GGT  TCA  TTA  ATT  GAA  ACT  GGT  GAA  AGA  TGT      48
Leu  Gly  Asn  Ile  Asp  Gln  Gly  Ser  Leu  Ile  Glu  Thr  Gly  Glu  Arg  Cys
 1                  5                   10                  15

GTT  TTA  ACA  GTT  CCA  TCT  ACA  GAT  ATA  GAA  AAA  GAA  ATC  CTT  GAT  TTA      96
Val  Leu  Thr  Val  Pro  Ser  Thr  Asp  Ile  Glu  Lys  Glu  Ile  Leu  Asp  Leu
                    20                  25                  30

GCT  GCT  GCT  ACA  GAA  AGA  TTA  AAT  TTA  ACT  GAT  GCA  TTA  AAC  TCA  AAT     144
Ala  Ala  Ala  Thr  Glu  Arg  Leu  Asn  Leu  Thr  Asp  Ala  Leu  Asn  Ser  Asn
                35                  40                  45

CCA  GCT  GGT  AAT  TTA  TAT  GAT  TGG  CGT  TCT  TCT  AAC  TCA  TAC  CCT  TGG     192
```

| Pro | Ala | Gly | Asn | Leu | Tyr | Asp | Trp | Arg | Ser | Ser | Asn | Ser | Tyr | Pro | Trp |
|-----|-----|-----|-----|-----|-----|-----|-----|-----|-----|-----|-----|-----|-----|-----|-----|
|     | 50  |     |     |     |     | 55  |     |     |     |     | 60  |     |     |     |     |

| ACT | CAA | AAG | CTT | AAT | TTA | CAC | TTA | ACA | ATT | ACA | GCT | ACT | GGA | CAA | AAA | 240 |
|-----|-----|-----|-----|-----|-----|-----|-----|-----|-----|-----|-----|-----|-----|-----|-----|-----|
| Thr | Gln | Lys | Leu | Asn | Leu | His | Leu | Thr | Ile | Thr | Ala | Thr | Gly | Gln | Lys |     |
| 65  |     |     |     |     | 70  |     |     |     | 75  |     |     |     |     |     | 80  |     |

| TAT | AGA | ATC | TTA | GCT | AGC | AAA | ATT | GTT | GAT | TTT | AAT | ATT | TAT | TCA | AAT | 288 |
|-----|-----|-----|-----|-----|-----|-----|-----|-----|-----|-----|-----|-----|-----|-----|-----|-----|
| Tyr | Arg | Ile | Leu | Ala | Ser | Lys | Ile | Val | Asp | Phe | Asn | Ile | Tyr | Ser | Asn |     |
|     |     |     |     | 85  |     |     |     |     | 90  |     |     |     |     | 95  |     |     |

| AAT | TTT | AAT | AAT | CTA | GTG | AAA | TTA | GAA | CAG | TCC | TTA | GGT | GAT | GGA | GTA | 336 |
|-----|-----|-----|-----|-----|-----|-----|-----|-----|-----|-----|-----|-----|-----|-----|-----|-----|
| Asn | Phe | Asn | Asn | Leu | Val | Lys | Leu | Glu | Gln | Ser | Leu | Gly | Asp | Gly | Val |     |
|     |     |     | 100 |     |     |     |     | 105 |     |     |     |     | 110 |     |     |     |

| AAA | GAT | CAT | TAT | GTT | GAT | ATA | AGC | TTA | GAT | GCT | GGA | CAA | TAT | GTT | CTT | 384 |
|-----|-----|-----|-----|-----|-----|-----|-----|-----|-----|-----|-----|-----|-----|-----|-----|-----|
| Lys | Asp | His | Tyr | Val | Asp | Ile | Ser | Leu | Asp | Ala | Gly | Gln | Tyr | Val | Leu |     |
|     |     | 115 |     |     |     |     | 120 |     |     |     |     | 125 |     |     |     |     |

| GTA | ATG | AAA | GCT | AAT | TCA | TCA | TAT | AGT | GGA | AAT | TAC | CCT | TAT | TCA | ATA | 432 |
|-----|-----|-----|-----|-----|-----|-----|-----|-----|-----|-----|-----|-----|-----|-----|-----|-----|
| Val | Met | Lys | Ala | Asn | Ser | Ser | Tyr | Ser | Gly | Asn | Tyr | Pro | Tyr | Ser | Ile |     |
|     | 130 |     |     |     |     | 135 |     |     |     |     | 140 |     |     |     |     |     |

| TTA | TTT | CAA | AAA | TTT | TAA | 450 |
|-----|-----|-----|-----|-----|-----|-----|
| Leu | Phe | Gln | Lys | Phe |     |     |
| 145 |     |     |     |     | 150 |     |

(2) INFORMATION FOR SEQ ID NO:2:

(i) SEQUENCE CHARACTERISTICS:
        (A) LENGTH: 149 amino acids
        (B) TYPE: amino acid
        (D) TOPOLOGY: linear (ii) MOLECULE TYPE: protein (xi) SEQUENCE DESCRIPTION: SEQ ID NO:2:

| Leu | Gly | Asn | Ile | Asp | Gln | Gly | Ser | Leu | Ile | Glu | Thr | Gly | Glu | Arg | Cys |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Val | Leu | Thr | Val | Pro | Ser | Thr | Asp | Ile | Glu | Lys | Glu | Ile | Leu | Asp | Leu |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Ala | Ala | Ala | Thr | Glu | Arg | Leu | Asn | Leu | Thr | Asp | Ala | Leu | Asn | Ser | Asn |
|-----|-----|-----|-----|-----|-----|-----|-----|-----|-----|-----|-----|-----|-----|-----|-----|
|     |     | 35  |     |     |     |     | 40  |     |     |     |     | 45  |     |     |     |

| Pro | Ala | Gly | Asn | Leu | Tyr | Asp | Trp | Arg | Ser | Ser | Asn | Ser | Tyr | Pro | Trp |
|-----|-----|-----|-----|-----|-----|-----|-----|-----|-----|-----|-----|-----|-----|-----|-----|
|     | 50  |     |     |     |     | 55  |     |     |     |     | 60  |     |     |     |     |

| Thr | Gln | Lys | Leu | Asn | Leu | His | Leu | Thr | Ile | Thr | Ala | Thr | Gly | Gln | Lys |
|-----|-----|-----|-----|-----|-----|-----|-----|-----|-----|-----|-----|-----|-----|-----|-----|
| 65  |     |     |     |     | 70  |     |     |     | 75  |     |     |     |     |     | 80  |

| Tyr | Arg | Ile | Leu | Ala | Ser | Lys | Ile | Val | Asp | Phe | Asn | Ile | Tyr | Ser | Asn |
|-----|-----|-----|-----|-----|-----|-----|-----|-----|-----|-----|-----|-----|-----|-----|-----|
|     |     |     |     | 85  |     |     |     |     | 90  |     |     |     |     | 95  |     |

| Asn | Phe | Asn | Asn | Leu | Val | Lys | Leu | Glu | Gln | Ser | Leu | Gly | Asp | Gly | Val |
|-----|-----|-----|-----|-----|-----|-----|-----|-----|-----|-----|-----|-----|-----|-----|-----|
|     |     |     | 100 |     |     |     |     | 105 |     |     |     |     | 110 |     |     |

| Lys | Asp | His | Tyr | Val | Asp | Ile | Ser | Leu | Asp | Ala | Gly | Gln | Tyr | Val | Leu |
|-----|-----|-----|-----|-----|-----|-----|-----|-----|-----|-----|-----|-----|-----|-----|-----|
|     |     | 115 |     |     |     |     | 120 |     |     |     |     | 125 |     |     |     |

| Val | Met | Lys | Ala | Asn | Ser | Ser | Tyr | Ser | Gly | Asn | Tyr | Pro | Tyr | Ser | Ile |
|-----|-----|-----|-----|-----|-----|-----|-----|-----|-----|-----|-----|-----|-----|-----|-----|
|     | 130 |     |     |     |     | 135 |     |     |     |     | 140 |     |     |     |     |

| Leu | Phe | Gln | Lys | Phe |
|-----|-----|-----|-----|-----|
| 145 |     |     |     |     |

(2) INFORMATION FOR SEQ ID NO:3:

(i) SEQUENCE CHARACTERISTICS:
        (A) LENGTH: 30 amino acids
        (B) TYPE: amino acid
        (C) STRANDEDNESS: single
        (D) TOPOLOGY: linear (ii) MOLECULE TYPE: peptide (v) FRAGMENT TYPE: C-terminal (vi) ORIGINAL SOURCE:
    (A) ORGANISM: Clostridium perfringens
    (B) STRAIN: NCTC 8239

(xi) SEQUENCE DESCRIPTION: SEQ ID NO:3:

```
Ser  Leu  Asp  Ala  Gly  Gln  Tyr  Val  Leu  Val  Met  Lys  Ala  Asn  Ser  Ser
1                  5                        10                       15

Tyr  Ser  Gly  Asn  Tyr  Pro  Tyr  Ser  Ile  Leu  Phe  Gln  Lys  Phe
               20                       25                  30
```

(2) INFORMATION FOR SEQ ID NO:4:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (iv) ANTI-SENSE: YES (xi) SEQUENCE DESCRIPTION: SEQ ID NO:4:

```
Asn  Thr  Asp  Gly  Ser  Thr  Asp  Tyr  Gly  Ile  Leu  Gln  Ile  Asp  Ser
1                  5                        10                       15
```